United States Patent
Arrizza et al.

(10) Patent No.: US 9,594,875 B2
(45) Date of Patent: Mar. 14, 2017

(54) MEDICAL DEVICE UPDATE SYSTEM

(71) Applicants: John Arrizza, Oceanside, CA (US);
James R. Shults, Ramona, CA (US);
Thomas J. Vaccaro, Encinitas, CA
(US); Patrick A. Ward, San Diego, CA
(US)

(72) Inventors: John Arrizza, Oceanside, CA (US);
James R. Shults, Ramona, CA (US);
Thomas J. Vaccaro, Encinitas, CA
(US); Patrick A. Ward, San Diego, CA
(US)

(73) Assignee: Hospira, Inc., Lake Forest, IL (US)

( * ) Notice: Subject to any disclaimer, the term of this patent is extended or adjusted under 35 U.S.C. 154(b) by 94 days.

(21) Appl. No.: 13/655,690

(22) Filed: Oct. 19, 2012

(65) Prior Publication Data

US 2013/0104120 A1    Apr. 25, 2013

Related U.S. Application Data

(60) Provisional application No. 61/549,826, filed on Oct. 21, 2011.

(51) Int. Cl.
*G06F 19/00* (2011.01)
*G06F 9/445* (2006.01)

(52) U.S. Cl.
CPC ............ *G06F 19/3412* (2013.01); *G06F 8/65* (2013.01); *G06F 19/3468* (2013.01)

(58) Field of Classification Search
CPC ..... G06F 8/60; G06F 8/61; G06F 8/62; G06F 8/63; G06F 8/64; G06F 8/65; G06F 8/66;
(Continued)

(56) References Cited

U.S. PATENT DOCUMENTS 4,213,454 A    7/1980    Shim
4,613,937 A    9/1986    Batty
(Continued)

FOREIGN PATENT DOCUMENTS

JP    2008158622 A    7/2008
WO    2010053703 A1    5/2010

OTHER PUBLICATIONS

Medfusion Syringe Infusion Pump Model 4000 Operator's Manual v1.1, medfusion, Sep. 2011, 153 pages, [retrieved on Mar. 19, 2015], Retrieved from the Internet: <URL:http://www.medfusionpump.com/assets/literature/manuals/Operators_Manual_4000_40-5760-51A.pdf>.*

(Continued)

*Primary Examiner* — Geoffrey St Leger
(74) *Attorney, Agent, or Firm* — Michael R. Crabb

(57) ABSTRACT

A system and method for providing updates to medical devices is disclosed. In one example, the medical devices are configured to pull update files in response to the reception of an update message from a server. Once the update files are downloaded by a medical device, the update files can be installed. While the medical device pulls the update files, the medical device can continue with its normal operation. If desired, a user can select which medical devices should be updated, based on any desired factors, such as the physical location of the device, the model of the device, the type of device, and the way the device is being used.

20 Claims, 16 Drawing Sheets

(58) Field of Classification Search
CPC ... G06F 8/665; G06F 8/67; G06F 8/68; G06F 8/70; G06F 8/71; G06F 19/3412; G06F 19/3468; A61M 5/168; A61M 5/172; A61M 31/002
See application file for complete search history.

(56) References Cited

U.S. PATENT DOCUMENTS

| | | | |
|---|---|---|---|
| 5,102,392 A | | 4/1992 | Sakai et al. |
| 5,177,993 A | | 1/1993 | Beckman et al. |
| 5,256,157 A | | 10/1993 | Samiotes et al. |
| 5,376,070 A | * | 12/1994 | Purvis et al. .......... 604/31 |
| 5,515,713 A | | 5/1996 | Saugues et al. |
| 5,681,285 A | | 10/1997 | Ford et al. |
| 5,713,856 A | | 2/1998 | Eggers |
| 6,151,643 A | | 11/2000 | Cheng et al. |
| 6,167,567 A | | 12/2000 | Chiles et al. |
| 6,249,705 B1 | | 6/2001 | Snell |
| 6,269,340 B1 | | 7/2001 | Ford et al. |
| 6,363,282 B1 | * | 3/2002 | Nichols .......... G06F 8/65 607/30 |
| 6,578,002 B1 | | 6/2003 | Derzay et al. |
| 6,681,003 B2 | | 1/2004 | Linder et al. |
| 7,060,031 B2 | | 6/2006 | Webb et al. |
| 7,069,552 B2 | | 6/2006 | Lindberg et al. |
| 7,167,755 B2 | | 1/2007 | Seeberger et al. |
| 7,383,088 B2 | | 6/2008 | Spinelli et al. |
| 7,471,994 B2 | | 12/2008 | Ford et al. |
| 7,565,197 B2 | | 7/2009 | Haubrich et al. |
| 7,697,994 B2 | | 4/2010 | VanDanacker |
| 7,856,276 B2 | | 12/2010 | Ripart et al. |
| 7,895,053 B2 | | 2/2011 | Holland et al. |
| 7,938,796 B2 | | 5/2011 | Moubayed |
| 8,352,290 B2 | | 1/2013 | Bartz et al. |
| 8,387,112 B1 | * | 2/2013 | Ranjan et al. .......... 726/2 |
| 2004/0215278 A1 | * | 10/2004 | Stegink .......... G06F 19/3412 607/30 |
| 2005/0080801 A1 | | 4/2005 | Kothandaraman et al. |
| 2005/0102669 A1 | * | 5/2005 | Marney et al. .......... 717/174 |
| 2005/0144043 A1 | | 6/2005 | Holland |
| 2006/0100746 A1 | | 5/2006 | Leibner-Druska |
| 2006/0106649 A1 | | 5/2006 | Eggers |
| 2006/0265186 A1 | * | 11/2006 | Holland .......... G06F 19/3468 702/182 |
| 2007/0027506 A1 | * | 2/2007 | Stender .......... G06F 19/3412 607/60 |
| 2007/0136098 A1 | | 6/2007 | Smythe |
| 2007/0233035 A1 | | 10/2007 | Wehba et al. |
| 2007/0233520 A1 | | 10/2007 | Wehba et al. |
| 2008/0052704 A1 | * | 2/2008 | Wysocki .......... G06F 8/65 717/173 |
| 2008/0133265 A1 | * | 6/2008 | Silkaitis et al. .......... 705/2 |
| 2008/0184219 A1 | | 7/2008 | Matsumoto |
| 2008/0320466 A1 | | 12/2008 | Dias |
| 2009/0069785 A1 | | 3/2009 | Miller |
| 2009/0099867 A1 | | 4/2009 | Newman |
| 2009/0157040 A1 | | 6/2009 | Jacobson et al. |
| 2009/0157695 A1 | | 6/2009 | Roberts |
| 2009/0158274 A1 | * | 6/2009 | Roberts .......... 717/178 |
| 2009/0171289 A1 | | 7/2009 | Davis et al. |
| 2010/0130933 A1 | | 5/2010 | Holland |
| 2010/0138523 A1 | | 6/2010 | Urness |
| 2010/0234708 A1 | | 9/2010 | Buck |
| 2010/0268157 A1 | | 10/2010 | Wehba et al. |
| 2011/0040158 A1 | | 2/2011 | Katz |
| 2011/0093284 A1 | | 4/2011 | Dicks |
| 2011/0093504 A1 | | 4/2011 | Butler |
| 2011/0264043 A1 | | 10/2011 | Kotnik et al. |
| 2011/0264044 A1 | | 10/2011 | Bartz et al. |
| 2011/0289497 A1 | * | 11/2011 | Kiaie et al. .......... 717/171 |
| 2012/0245554 A1 | | 9/2012 | Kawamura |
| 2013/0036412 A1 | * | 2/2013 | Birtwhistle .......... G06F 19/3412 717/171 |

OTHER PUBLICATIONS

SIGMA Spectrum operator's manual, SIGMA International, Oct. 8, 2009, 72 pages, Retrieved from the Internet: <URL:http://static.medonecapital.com/manuals/userManuals/Sigma-Spectrum-Operator-Manual-October-2009.pdf>.*

Infusomat Space and Accessories, Braun, Nov. 2010, 70 pages, Retrieved from the Internet: <URL:http://corp.bbraun.ee/Extranet/Infusioonipumbad/Kasutusjuhendid/Vanad/Kasutusjuhend-Infusomat_Space(vers688J,inglise_k).pdf>.*

Lor Siv-Lee et al., Implementation of Wireless "Intelligent" Pump IV Infusion Technology in a Not-for-Profit Academic Hospital Setting, Hospital Pharmacy, 2007, pp. 832-840, vol. 42, No. 9, Wolters Kluwer Health, Inc.

International Search Report for International Application No. PCT/US2012/061055, mailed Jan. 7, 2013.

* cited by examiner

FIG. 20

MEDICAL DEVICE UPDATE SYSTEM

FIELD

This disclosure relates in general to medical devices. More particularly, the present disclosure relates to a novel system and method for updating software and configuration files in medical devices, such as infusion pumps.

BACKGROUND

Intravenous infusion therapy is prescribed where it is desirable to administer medications and other fluids directly into the circulatory system of a patient. Some conventional infusion pumps are provided with a hospital customized drug library and warn the clinician when they are trying to enter or program a dose or other configuration parameter that is outside the recommended range of the established clinical practice of the hospital. There are various types of infusion pumps used by medical personnel to infuse medicinal fluids into a patient's body. As mentioned above, some pumps use a customized drug library for electronically downloadable drug pumps. For example United States Patent Application No. 2007/0213598, which is incorporated by reference herein in its entirety, describes a system for maintaining drug information and communicating with medication delivery devices. In addition to updating a customized drug library, it is often desirable to update software running on a medical device, such as an infusion pump. However, prior art systems have several drawbacks. Following is a description of a novel medical device update system that solves various problems found in the prior art.

SUMMARY

A method is described for providing updates to a medication administering device, the method including sending a message to the medication administering device, the message containing information relating to one or more update files available to the medication administering device, receiving the message at the medication administering device, downloading and storing one or more update files identified by the message, and installing the one or more update files on the medication administering device.

Another example provides a medical device system including a server, a communication network, and a plurality of medical devices in communication with the server over the communication network, the plurality of medical devices each having a storage location, and a control unit for controlling the operation of the medical device, wherein the control units are configured to pull update files in response to an update message received from the server, and wherein the control units are configured to manage the installation of downloaded update files.

Other features and advantages of the present disclosure will be apparent from the accompanying drawings and from the detailed description that follows below.

BRIEF DESCRIPTION OF THE DRAWINGS

The present disclosure is illustrated by way of example and not limitation in the figures of the accompanying drawings, in which like references indicate similar elements and in which:

FIG. 20 is a screenshot of an exemplary selection wizard used by a user to select software and drug library updates and devices to be updated.

DETAILED DESCRIPTION

Figure 1:
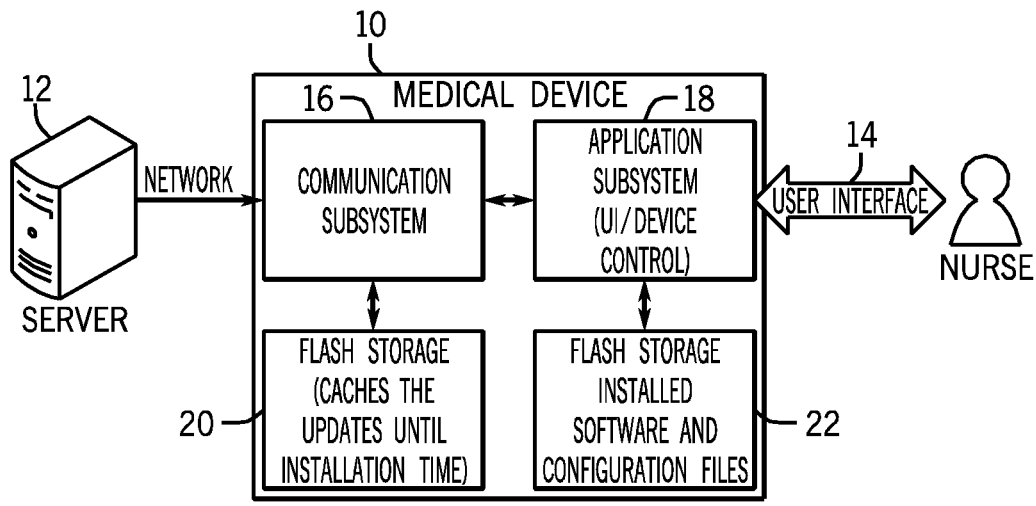
FIG. 1 is a block diagram illustrating a medical device in a hospital environment.

In general, the present disclosure describes a system and method for providing updates to medical devices or medical devices systems, such as medication administrating devices like medical infusion devices or infusion pumps. It is sometimes desirable to update the software running on a medical device to improve the performance, address problems, add features, or otherwise modify the operation of the medical device. For medical devices using a customized drug library, it is also sometimes desirable to update the drug library. In one example, software and configuration updates are "pulled" by the medical devices, rather than being "pushed" by a server (described in detail below).

While the system and methods described below may be applied to any desired medical device, the system and methods will be described in the exemplary context of infusion pumps. For example, the techniques disclosed may be used with infusion pumps such as a PLUM A+™ infuser or pump, available from Hospira, Inc. of Lake Forest, Ill. Other types of pumps may also be used with the present disclosure. For example, the techniques may be used with patient-controlled analgesia (PCA) pumps, ambulatory pumps, enteral pumps, as well as IV infusion pumps. Application of the present invention to other medical devices such as ventilators, imaging systems, patient physiological condition monitors, glucose meters, diagnostic equipment and the like is also contemplated.

When configuring systems to update medical devices, numerous factors should be considered. For example, sometimes updates to the software and to the configuration of medical devices deployed into clinical settings are difficult to achieve in a timely and coordinated manner. The costs in time and labor are significant, also there may be opportunities for confusion in that two otherwise identical medical devices may operate or behave in different ways if a staggered update process is implemented and different configurations and software are in operation side-by-side.

There are typically two types of update processes which are preformed on deployed medical devices. These two types of update processes include updates to the operational software of the medical device, and updates to the device configuration. In the example of an infusion pump, an update to the device configuration may include updates to a customized drug library, which may include but is not limited to defaults, ranges (hard and/or soft limits) of acceptable pump configuration parameters like dose, rate, and volume; device-specific settings; acceptable ranges of monitored values, etc.

The task of updating software for medical devices deployed in clinical settings has traditionally required that the medical devices be physically removed from the clinical floor and transported to a specially prepared location such as a biomed center (a location where pumps are cleaned and serviced). Once removed from the floor, the devices may require special configuration, or partial disassembly by manufacturers' technicians in preparation for the update process. The software updates are then applied by technicians using a special update station in the biomed center. Updated devices, which required disassembly, are then reassembled by the manufactures' technicians. If necessary, the device can be specially configured to allow for verification that the update is successful. Once an update has been verified, the device is reconfigured for the clinical floor, typically by the hospital biomed technician. The device is also cleaned, completing the update process. The device is now ready to be returned to the clinical floor.

The update process described above typically takes more than an hour per device and does not scale well due to the number of manual steps and limiting mechanical steps, such as the time spent in the special programming station. Updating a hospital with thousands of devices, for example, using such a process, will take a considerable amount of time and effort. For example, a hospital with 2000 devices takes approximately one man year of effort to update.

Updating the configuration of a medical device is typically performed more often than the updating the software for the medical device. In one example, the device configuration is customized by the hospital directly and is updated quarterly (or more often) by the hospital, without any interaction with or assistance from manufacturers' technicians. Of course, configuration updates can be performed more or less frequently, as desired. In addition, configuration updates can be performed by hospital personnel, manufacturers' technicians, or other users.

In many cases, the configuration of a medical device may be updated electronically, if the medical devices are networked. In one example, the mechanism used to electronically deploy these updates is to 'push' the update data in small packets from a central server to the medical devices which are being updated. One drawback to this approach is that this process is so resource intensive at the server, that it is typically only effective when preformed to small groups of medical devices at a time, perhaps fifteen devices, in one example. In some examples, the medical devices are removed from the clinical floor and placed into a special state by the biomed technician to allow the update to be transferred to the device. As with the software updates, these manual steps limit the number of devices which may be updated in a given period of time.

In the example of pushing configuration updates, a hospital IT technician will begin the update process by manually selecting the medical devices which are to be updated. The technician then waits for the transfer of configuration updates to the devices to complete before additional devices are selected. In one example, the transfer time to the devices may take approximately thirty minutes, although the transfer time can also take over an hour for large configuration files. Also, in some examples, this type of transfer requires that if the transfer fails for any reason, it must then start again from the beginning—regardless of how much of the configuration was correctly received by the device. This leads to lengthy deployment times and inefficient utilization of the IT technicians' time as they must monitor the process and wait for completion before scheduling additional medical devices to update. If the medical devices require a biomed technician interaction or assistance, such as getting the device into a specific mode to accept the configuration update, then the biomed technician's actions will need to be synchronized with the IT technicians, which is another drain on hospital resources.

As mentioned above, the present disclosure also describes a system and method for providing updates to medical devices, such as infusion pumps, by pulling updates at the medical devices, rather than pushing updates from a server. This approach allows medical devices to remain on the clinical floor during software and configuration updates. Updates performed in this manner are installed by the medical device itself, without requiring the disassembly, manual programming or other special handling by either manufactures' technicians or hospital biomed technicians. In this example, updates are transferred to the medical devices using the hospital networking infrastructure. Also, in some examples, the installation of updates on a medical device is triggered by a user, such as a nurse, or other hospital personnel.

FIG. 1 is a block diagram illustrating a medical device in a hospital environment. As shown in FIG. 1, a medical device 10 (for example, an infusion device) and a remote server 12 are coupled by a computer network, allowing the server and medical devices to communicate with one another. The server 12 could be located in the hospital, at a location away from the hospital, at a manufacturer's facility, in another hospital, or anywhere else, as desired. The medical device 10 includes a user interface 14, allowing a user (e.g., a doctor, nurse, technician, patient, etc.) to monitor and/or operate the medical device 10. The user interface may include displays, key pads, touch screens, buttons and knobs, audio indicators, etc. Also note that, as is described in detail below, updates from the server 12 may also be transferred to a medical device using a physical storage medium (e.g., a removable USB flash drive, etc.), rather than using the network. Also, a variety of communication networking methods could be used to accomplish the transfer depending on the networking infrastructure available; for example Ethernet, Wi-Fi and Cellular networks could all be used for this purpose.

FIG. 1 also shows several subsystems of the medical device 10. A communication subsystem 16 facilitates communications between the medical device 10 and the server 12, as well as between the medical device 10 and other devices. An application subsystem 18 controls the operation of the medical device 10, as well as user interface 14. The medical device 10 also has a plurality of storage locations (described below). In the example of FIG. 1, a first flash storage location 20 caches updates until the updates are installed. A second flash storage location 22 stores installed software and configuration files. The operation of the first and second flash storage locations 20 and 22 is described in detail below, but generally, when updates are downloaded, they are cached and installed at a later time. At the same time, the current software and configuration files are cached, and are available to the system in the event that an update fails. This way, the medical device can return to the operating state that it was in prior to an attempted update. Also note that the storage locations, as described above, are merely examples. More or less storage locations could be used. Also, any desired type of storage medium could be used, besides flash memory. For example, the storage locations could use hard drives, solid state drives, or any other type of non-volatile memory.

Figure 2:
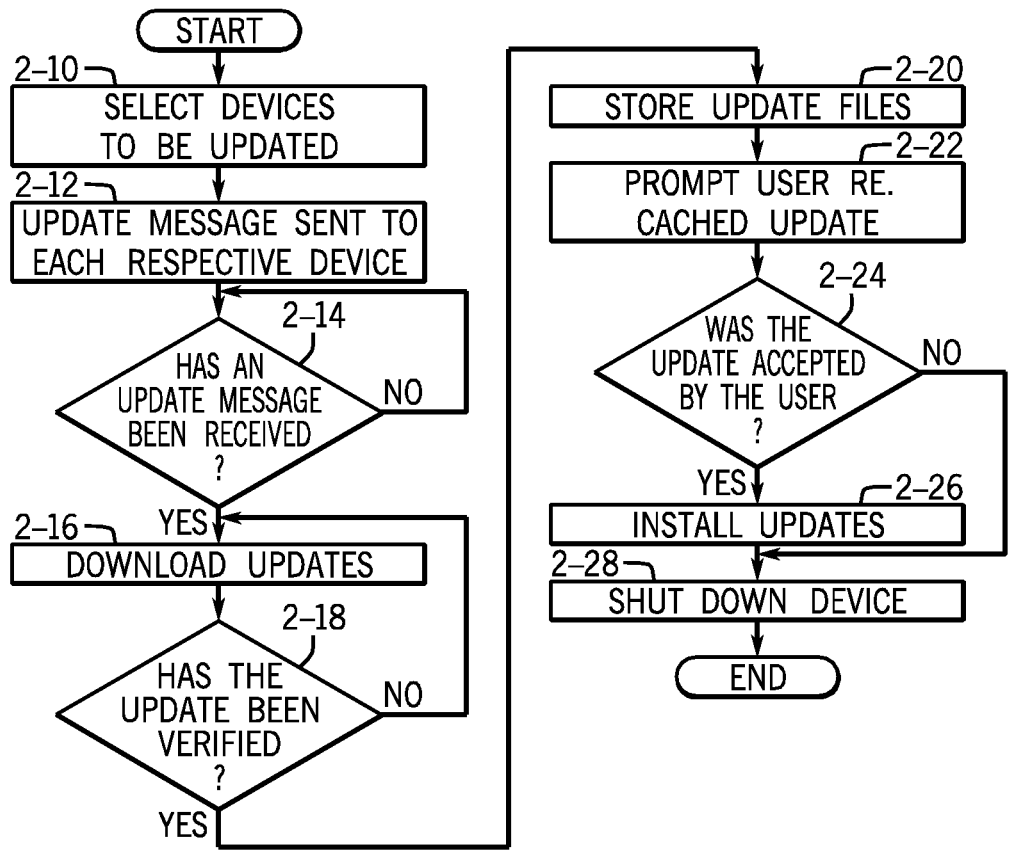
FIG. 2 is a flowchart illustrating one example of the process of updating a medical device.

FIG. 2 is a flowchart illustrating one example of the operation of a process of updating a medical device. The updating process is generally the same whether the software or configuration of the medical device is being updated.

The process illustrated in FIG. 2 begins at step 2-10 with a hospital IT technician (or other user) selecting the medical devices which are to be updated. Examples of the selection process are described in more detail below. After the medical device(s) are selected, the server will transmit an update message (in one example, a single message) over the network to each of the selected medical devices in the selected set of medical devices (step 2-12). In one example, each medical device receives a unique message. In other examples, the same message can be sent to the devices, with each device being able to parse the information relevant to that particular device. Devices that are not actively connected to the network will receive the update message when the server reestablishes communication with the device. In one example, the update message contains information about the update that the medical device will need to download and install the update. For example, the update message may identify the files that make up the update as well as the files' location on the network. One reason for this is to eliminate scaling issues which might otherwise force the server to manage the segmentation and transfer of updates to the devices at the application level.

At step 2-14, the process determines whether an update message has been received by the communication subsystem. If an update message has not been received, the process will keep waiting for a message. If an update message has been received, the process continues. At this point, the medical devices are now responsible for downloading the files of the update using networking operating system level interfaces, rather than an application level interface directly to each device. This distributes the workload to the devices (rather than being a burden on the server); with the further advantage of allowing the update file transfer to resume from a point when the network connection is lost to when it is reestablished. The continuing download can be accomplished without starting the process over.

At step 2-16, the update identified in the received update message is downloaded or pulled by the medical device. At step 2-18, the process determines whether the downloaded update has been verified. In one example, a downloaded update can be verified by using a checksum, or by using any other desired verification method. If the downloaded update files cannot be verified, the process proceeds back to step 2-16, where the updates are downloaded again. As mentioned before, the download process can continue where it left off, and the entire download process does not need to be restarted. Once the update is verified as being transferred correctly, the update files are stored in the storage location (step 2-20) by the communication subsystem, until needed by the installation process. In one example, at this point, the medical device waits for a signal from a user (e.g., a nurse, caregiver, or patient, etc.) to begin the installation process.

After the updates files are downloaded, verified, and stored, the communication subsystem signals to the application subsystem that an update is available. At this point, the system waits until such time that the updates can be installed. In one example, updates can be performed during a device power off process. In this example, when a user (e.g., a nurse, caregiver or patient) powers off the medical device, the user interface will prompt the user (step 2-22) with the information that an update (software, configuration, or both) is cached in the communication subsystem, and may now be installed. The process then proceeds to step 2-24, where the process determines whether the user accepts the update or rejects the update. If the user accepts the update, the installation process (step 2-26) will begin automatically. Once the update is complete, the device will shutdown normally (step 2-28). If, at step 2-24, the user rejects the update, the medical device will shutdown normally, without installing the update. The user interface will continue to notify the user of the available update until it is accepted. Throughout the update process described above, the status of the update process (e.g., update message received, update downloaded, update installed, update failed, etc.) is sent to the server by the communication subsystem. This way, the server will be able to track the status if each medical device in the system. If the medical device is unable to communicate with the server, the device will inform the server of its status when communication is established at a future later time. Similar status messages can be displayed on the user interface of the medical device.

Also note that, in one example, steps 2-10 through 2-20 can be performed in the background while the medical device is operating in its normal manner. As a result, the device does not need to be pulled from the clinical floor or placed into a special update mode in order to download and cache update files. In the example of an infusion pump, updates can be downloaded and stored at the same time that the infusion pump is being used to administer medications to a patient, without affecting the normal operation of the infusion pump. Also note that the process illustrated in FIG. 2 is described in the context of a single medical device. However, the update system can use the same process to administer updates to many of devices at the same time.

Following is a more detailed description of an exemplary update processes. Of course, updates may be performed in numerous ways, within the scope of this disclosure.

As mentioned above, an early step in the update process is to select one or more medical devices to be updated. Devices can be selected individually, or in groups, sets or subsets based on device type, device model, device location, etc. In one exemplary implementation of this feature, a wizard-based selection mechanism (described below) is provided to allow any number of the devices to be selected for updates. The wizard can run on the server, or on a network client that communicates with the server. Once an update process is triggered, the status of the update as it progresses will be displayed using the user interface of the server or network client, and will be available for viewing, and for use in standard reports.

One benefit of the update process illustrated in FIG. 2 relates to scalability. As mentioned above, as device update systems are scaled up, the load on a server can be overwhelming, preventing devices from being updated in a timely, cost-effective manner. By utilizing the 'pull' updating process illustrated in FIG. 2, an update process can be easily scaled up, without overwhelming the server. To help understand the differences between the 'push' technique mentioned above and the 'pull' technique illustrated in FIG. 2, a brief explanation of each technique is provided below.

Figure 3:
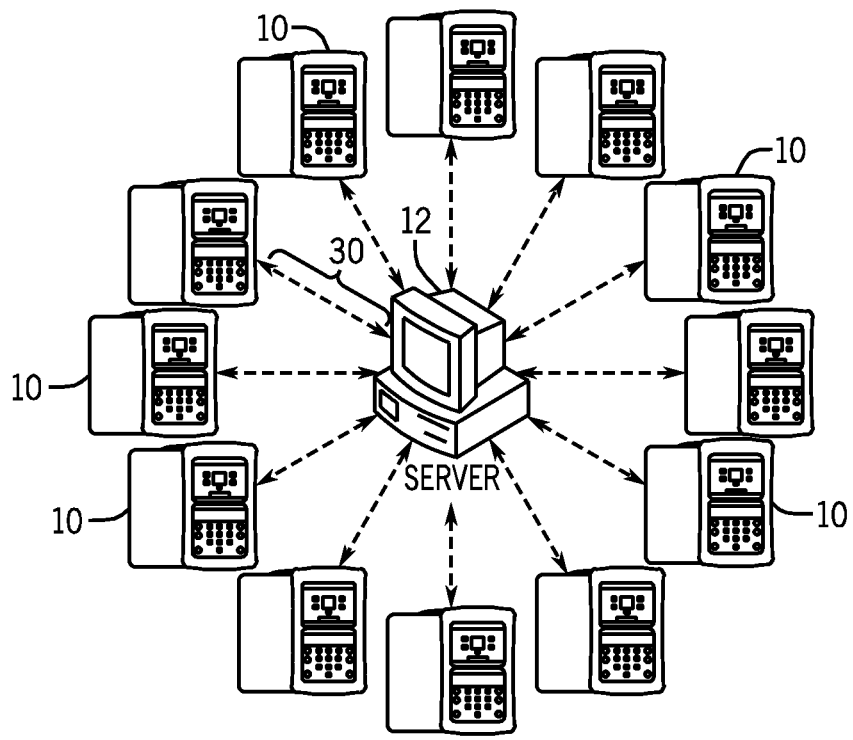
FIG. 3 is a block diagram of an update system using a 'push' update technique.

FIG. 3 is a block diagram of an update system using a 'push' update technique. FIG. 3 shows a server 12 and a plurality of medical devices 10, which are capable of communicating with the server 12 over a network. When a device 10 is selected for an update, the server 12 will segment the software or configuration file(s) into a plurality of chunks 30, and will calculate a checksum over the first chunk 30, which will be used later by the respective device 12 to verify that the transfer of the chunks 30 was completed without corruption or error. The server 12 opens and maintains a connection to the device 12 across the network. During an update process, each of the chunks 30 will be individually sent to the respective device 10. The server 12 monitors the delivery status of each chunk.

The device 10 receives and verifies each chunk 30 and sends a delivery success or delivery failure message to the server 12. The server 12 will then prepare, checksum, and send the next chunk 30. This process will repeat until the entire update file(s) has been transferred correctly or has failed. The failure recovery for this technique is to start over with the download beginning with the first chunk.

Using the example shown in FIG. 3, the load on the server 12 to segment and track the files as they are pushed to the medical devices is quite high, and may quickly saturate the server 12. As a result, perhaps only a few devices can be updated simultaneously, in order to maintain adequate resources to service devices that are not being updated. For example, the server receives status and log information from the devices and communicates therapy programming information to the devices, and is hampered in those activities.

Figure 4:
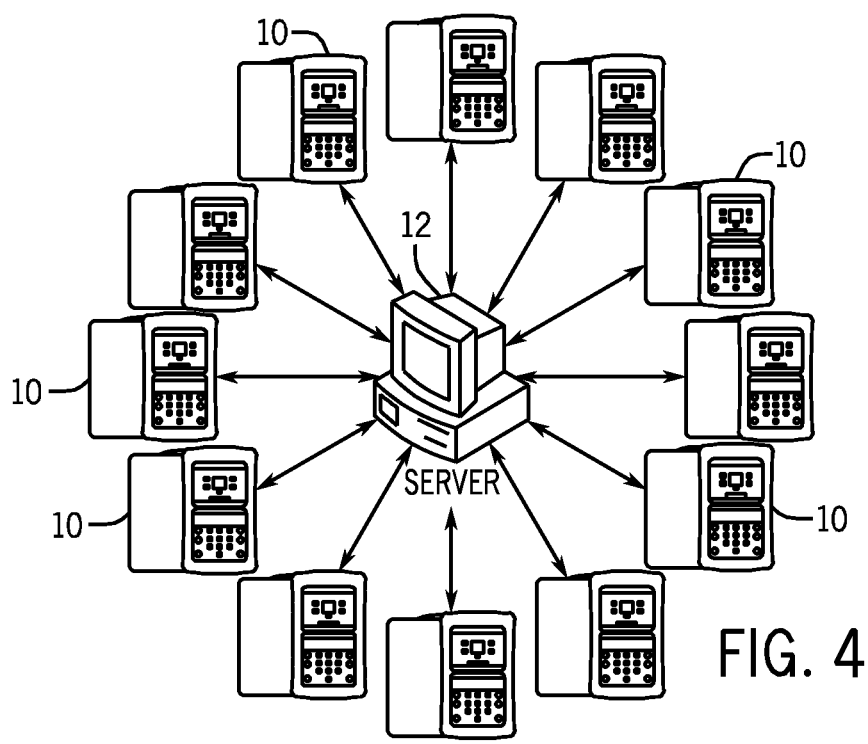
FIG. 4 is a block diagram of an update system using a 'pull' update technique

FIG. 4 is a block diagram of an update system using a 'pull' update technique, such as that described with respect to FIG. 2. FIG. 4 shows a server 12 and a plurality of medical devices 10, which are capable of communicating with the server 12 over a network. Using this method, in comparison to the method illustrated in FIG. 3, the server 12 sends to each medical device 10 to be updated an update message, which contains the location of files which makeup the update, called a manifest. From this point on, the medical devices themselves are responsible for downloading the update files. This results in a dramatic reduction in the amount of work the server 12 is responsible for at the application layer. A direct result of this is linear scalability of the update system, to the limit of system resources, chiefly network bandwidth.

Should the transfer of an update file fail, the device 10 automatically resumes the transfer from the point of the failure, rather than starting the download over. In this example, the device 10 will inform the server 12 of the status of the transfer. This messaging exchange provides only a light load on the server 12, freeing the server 12 to service the above-mentioned needs of the devices which are not being updated.

An additional improvement with this technique is that the manifest contains a checksum and version information. Therefore, the files which are already present on the device 10 are not transferred again. This will improve network utilization and system performance. Note that the same technique is used for software updates as well as for configuration updates.

Figure 5:
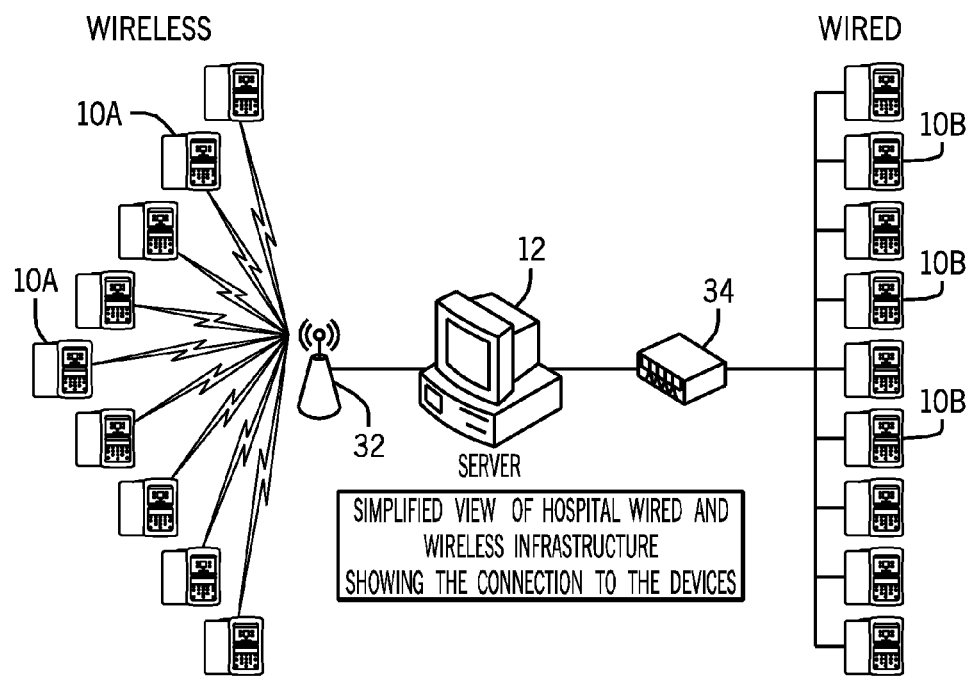
FIG. 5 is a block diagram showing a high level view of a hospital network.

The update mechanism described above supports wired and wireless infrastructures in a medical facility. FIG. 5 is a block diagram showing a high level view of a hospital network, including both wired and wireless connections to medical devices which may receive updates. FIG. 5 shows a server 12 coupled to a wireless router 32 for communicating with a plurality of medical devices 10A that have a wireless interface with the network. The server 12 is also coupled to a wired network router 34 for communicating with a plurality of medical devices 10B that have a wired interface with the network. Note that the network configuration shown is merely an example, and that other network configurations may also be used. Also, as described below, a medical device may also receive update files using a physical storage medium, such as a removable disk or USB flash drive.

Figure 6:
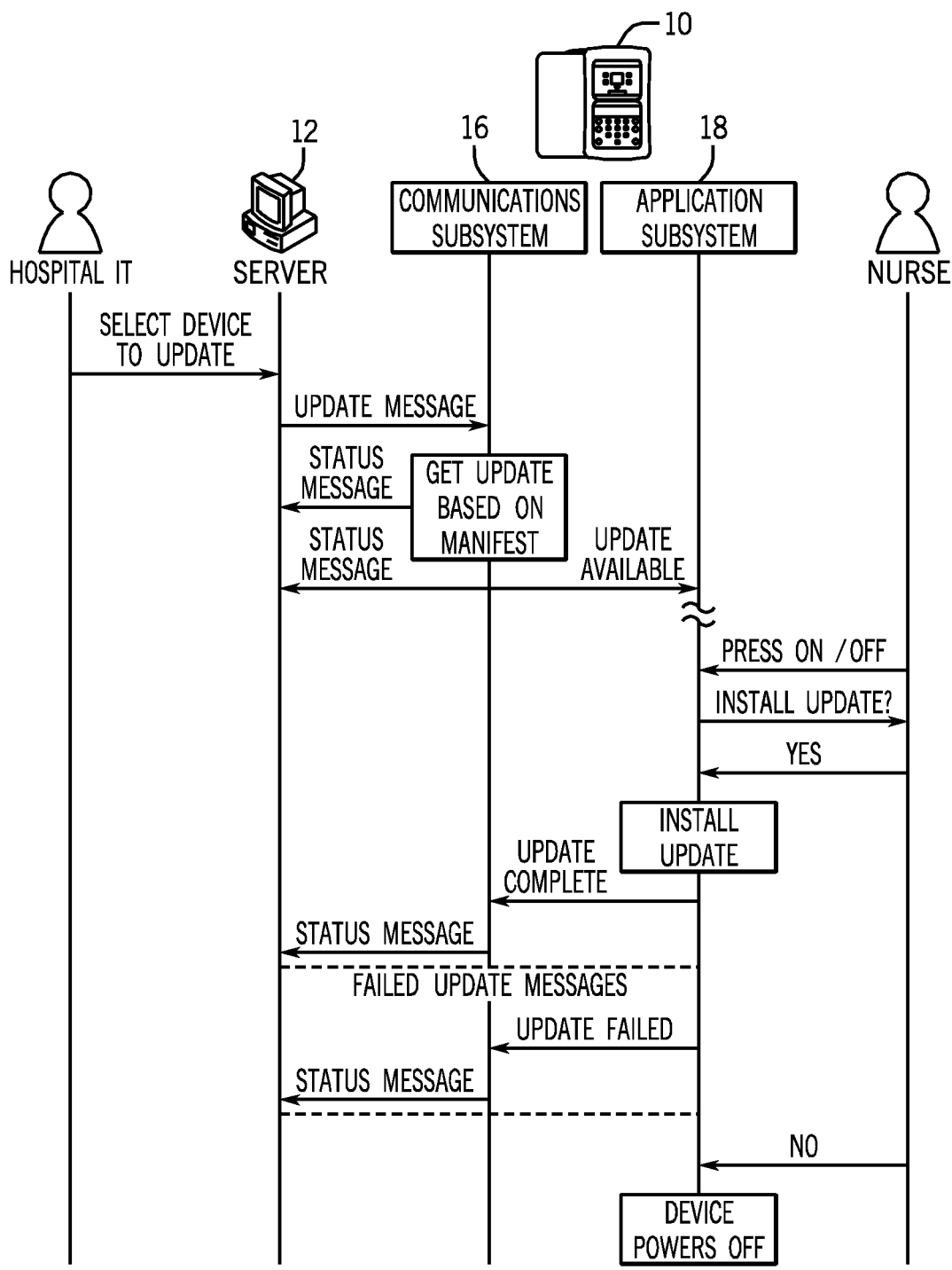
FIG. 6 is a sequence diagram illustrating an example of an update process.

FIG. 6 is a sequence diagram illustrating an example of the high level message handling and actions for the update process described above. FIG. 6 shows the server 12 and medical device 10 (including the communication subsystem 16 and application subsystem 18) described above with respect to FIG. 1. FIG. 6 also illustrates the actions of a first user (shown as hospital IT personnel) and a second user (shown as a nurse, caregiver or patient) in the process.

As shown, a first user selects one or more devices to be updated (software and/or configuration updates). In response, the server 12 generates and sends an update message for the medical device 10. The update message contains the network location of the update files. The communication subsystem 16 receives the update message and in response, downloads the update files (checking any files it already has against the manifest in the update). Once the files are downloaded and verified to have been transferred correctly, the communication subsystem will write the files to local flash storage to cache them on the device 10, awaiting the time when the user initiates the update process. When all of the update files are cached, the communication subsystem 16 will send a message to the application subsystem 18, indicating that an update is available.

During a normal shutdown of the medical device the application subsystem 18 will ask the user (a nurse, in this example) whether the updates should be installed. If the user accepts, the updates will be installed, and the medical device 10 will shutdown. During the updating process, the medical device will provide status messages to the server 12, indicating the status of the update process (e.g., files successfully downloaded, download failed, update complete, update failed, etc.).

As mentioned above with respect to FIG. 1, the medical device 10 also has first and second flash storage locations 20 and 22 for caching updates and installed and configuration files. In one example, the storage locations can be utilized as follows.

After an update has been downloaded and the files have been cached, the communication subsystem 16 advertises the availability of the update to the application subsystem 18. As such, there is a window during which the update has not been transferred to the application subsystem 18. During the window, if a new update (i.e., a second new update) is transferred to the communication subsystem 16, it should also be verified and stored. Until this process is complete, the previous update is considered the active update, and will be what is sent to the application subsystem 18, if an update is requested by the user.

However, once the new update (the second new update) is successfully transferred from the server and written to the alternate cache location, this new update (the second new update) becomes the active update, and will be what is sent to the application subsystem if an update is requested by the user.

Figure 7:
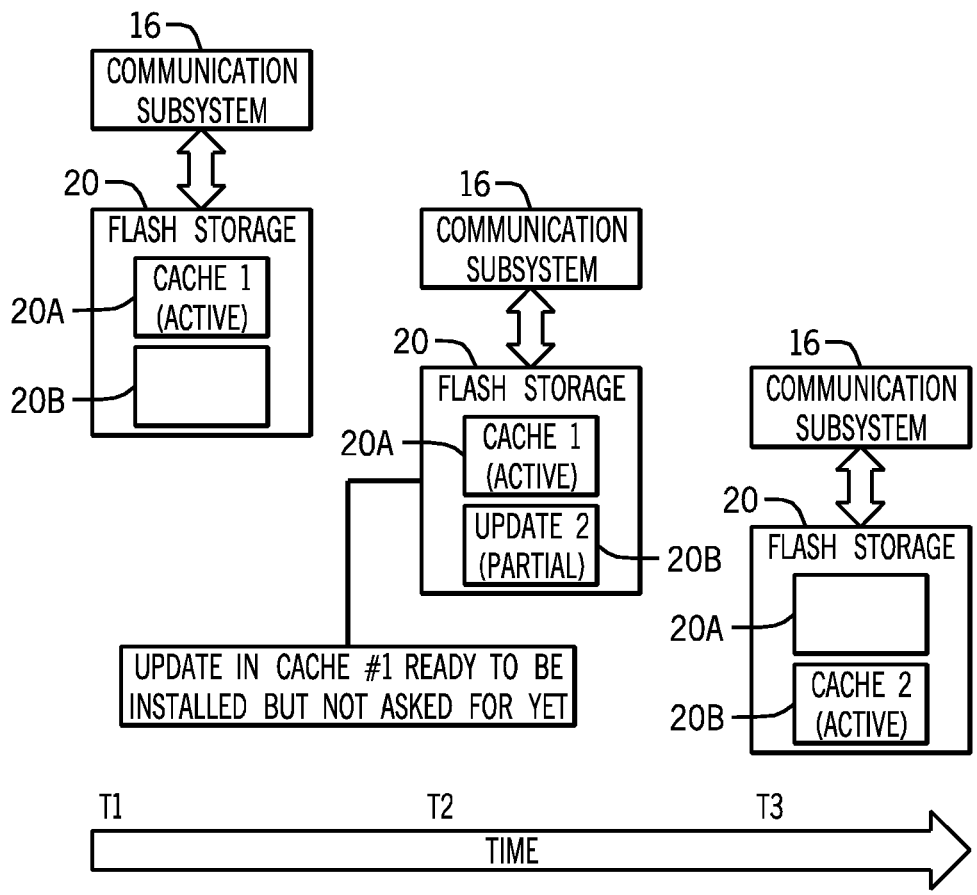
FIG. 7 is a timing diagram showing a process where two new updates are downloaded prior to installation.

FIG. 7 is a timing diagram showing this process (where 2 new updates are downloaded). FIG. 7 shows the communication subsystem 16 and the storage location 20 at three different time periods—T1, T2, and T3. The storage location 20 includes two partitions (cache locations 20A and 20B). At time T1, a first update has been downloaded and stored in storage location 20A. At time T1, this update is considered the active update, meaning that, if an update request were to come from the user at time T1, that is the update that would be installed.

At time T2, the first update is still cached, but there has still been no request from a user to install the update. At the same time, a newer update (a second new update) is currently downloading to storage location 20B. At time T2, the first update (the stored in cache 20A) is still considered the active update, meaning that, if an update request were to come from the user at time T2, that is the update that would be installed.

At time T3, the second new update has finished downloading, has been verified, and is stored in storage location 20B. Now, since this update is the newest, this update is considered the active update, and would replace the previous uninstalled update. If an update request were to come from the user after time T3, the second update (stored in storage location 20B) would be the update that would be installed. This situation may be a rare, but possible circumstance.

To ensure the continued proper operation of a medical device, precautions should be taken to maintain the proper operation software and/or configuration of the medical device. For example, some medical devices cannot operate without a correct configuration. In this case, special care can be taken to preserve the previous configuration (if it is still acceptable) when a configuration update installation fails. In one example, when updates are transferred from the communication subsystem, until they are successfully received and committed to flash, the previous configuration remains in effect.

Once the new updated configuration is committed to flash, the former configuration is deactivated and becomes the previous configuration and this location is where the next new configuration will be written. If the receipt of a new configuration fails, or if the write to flash of the new configuration fails, then the active partition remains unchanged. If the receipt and write are successful, then the new configuration becomes the active configuration.

Figure 8:
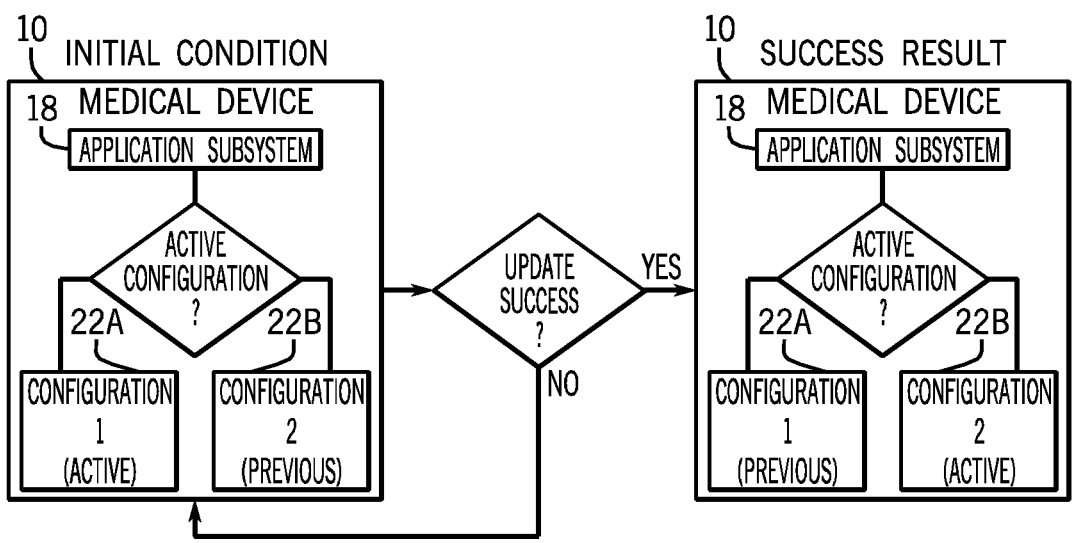
FIG. 8 is a diagram and flow chart illustrating the state of a medical device before and after an attempted update.

FIG. 8 is a diagram and flow chart illustrating the state of a medical device before and after an update. The left portion of FIG. 8 shows the medical device in an initial condition. In the initial condition (the left side), two configurations are cached, the active configuration (stored in storage location 22A), and the previous configuration (stored in storage location 22B). If the installation of new configuration is successful (the right side of FIG. 8), the new configuration becomes the active configuration, and the former configuration is deactivated and becomes the previous configuration (this is where the next new configuration will be written). If the installation of new configuration fails, then the active partition remains unchanged.

In one example, the processing of updates follows a script which is contained in the update message. The communication subsystem uses the script to orchestrate the processes and sequences which will be followed. For example, the script may dictate which portions of the system are updated first and how they are updated. The system may also provide for some flexibility in the update process to counter unforeseen issues.

In one example, the scripting can be used to force the update to occur during the power off processing without offering the option to a user to not perform or defer the update. In other words, the assent of the user is not required. This may be useful in a situation where an update is very important, or if the update fixes a known problem with the medical device.

In another example, the scripting can be used to have an update be staged on the device until a specific time, so that all updates would be available after a specific time in the future, but not before. In another example, the scripting can be used to ensure an update is installed by a certain date and/or time, or on a specific date and/or time. Scripting may also be used for numerous other features, as desired.

Since the proper operation of a medical device is very important, some measures should be taken to ensure that updates are performed securely. The security of the update files is insured by encrypting the update file in such a way that the medical device will be able to decrypt the files after transfer. However, if update files are intercepted during transfer it would be impossible to view the data in the update. Any desired conventional encryption scheme could be used.

The encryption mechanism will also insure that if an update file is intercepted, it cannot be modified and then replayed to the medical device as a valid update. If attempted, the device will reject the update as an invalid file. Only correctly encrypted files will be accepted by the medical device as the most basic level of integrity check on the update that is transferred.

As mentioned above, in other examples of the basic mechanism for software and configuration updates is an extension to a physical device for transport of the updates, rather than utilizing the hospital network infrastructure. While any desired physical device may be used, an example will be described using a USB flash disk. In this example, the server creates and stores an update(s) on a USB flash disk which will contain the update files and an associated script. When the USB flash drive is inserted into a device to be updated, the communications subsystem will copy the update files from the USB interface just as if the update was transferred across the network infrastructure.

Figure 9:
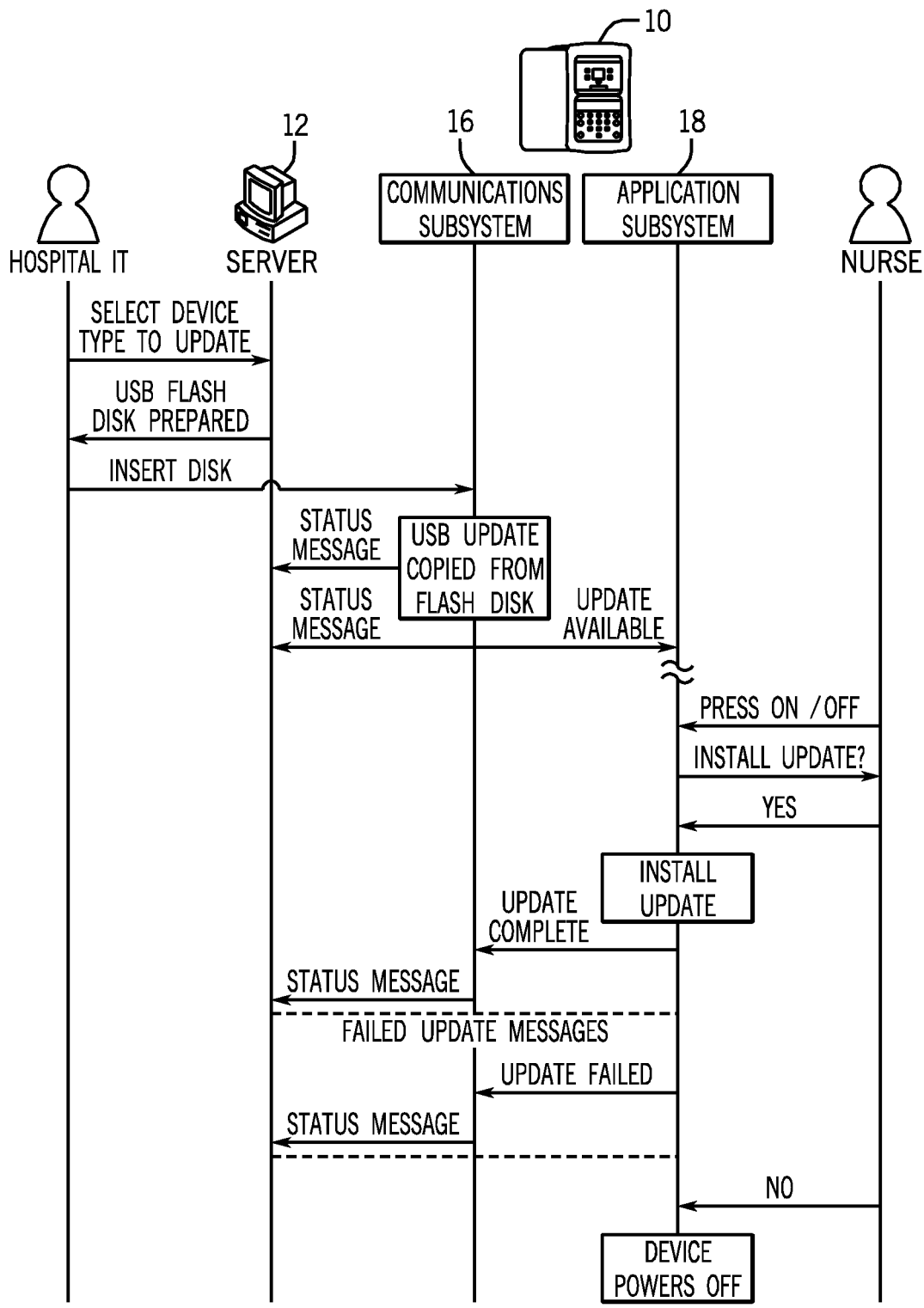
FIG. 9 is a sequence diagram illustrating an example of the high level message handling and actions for an update process using a removable USB flash drive.

If the medical device is networked, it will continue to operate as it would for a network delivered update and report the status of the update as it occurs. FIG. 9 is a sequence diagram illustrating an example the high level message handling and actions for an update process using a USB flash disk to transport updates. FIG. 9 shows the server 12 and medical device 10 (including the communication subsystem 16 and application subsystem 18) described above with respect to FIG. 1. FIG. 9 also illustrates the actions of a first user (shown as hospital IT personnel) and a second user (shown as a nurse) in the process.

As shown, a first user selects a device or device type to be updated (software and/or configuration updates). In response, the server generates a USB flash disk that contains the update(s) and the script. At the medical device 10, a user inserts the USB disk into a USB port on the device 10. At this point, the script takes over, and the update is copied by the communications subsystem 16. Once the files are copied from the flash disk and verified, the update files will be stored in cache, awaiting the time when the second user initiates the update process. When the update files are cached, the communication subsystem 16 will send a message to the application subsystem 18, indicating that an update is available.

During a normal shutdown of the medical device 10, the application subsystem 18 will ask the user (a nurse, in this example) whether the updates should be installed. If the nurse accepts, the updates are installed, and then the medical device 10 will shutdown. During the updating process, the medical device will provide status messages to the server 12 (assuming that the device 10 is networked), indicating the status of the update process (e.g., files successfully downloaded, download failed, update complete, update failed, etc.). If the medical device 10 is not networked, the status messages will be sent to the server the next time the device is connected to the network.

The description above of a medical device update system has been described in general terms, with some more specific examples included. Following is a description illustrating an exemplary implementation in specific medical device system. The following description describes a system based upon Plum A+™ infusion pumps and Hospira MedNet™ software working together through a network system in a hospital environment. Plum A+™ infusion pumps and Hospira MedNet™ software are available from Hospira, Inc. of Lake Forest, Ill. and can be adapted or modified according to the present invention.

An infusion pump system is provided for delivering and installing a drug libraries and infusion pump software electronically. The installation of software is integrated with a drug library download and installation process. Described below are representations of the display screens and actions that occur during software and drug library installations, including for both success and failed installations. Sequence diagrams show at a high level the interaction and interface with the various systems.

Figure 10:
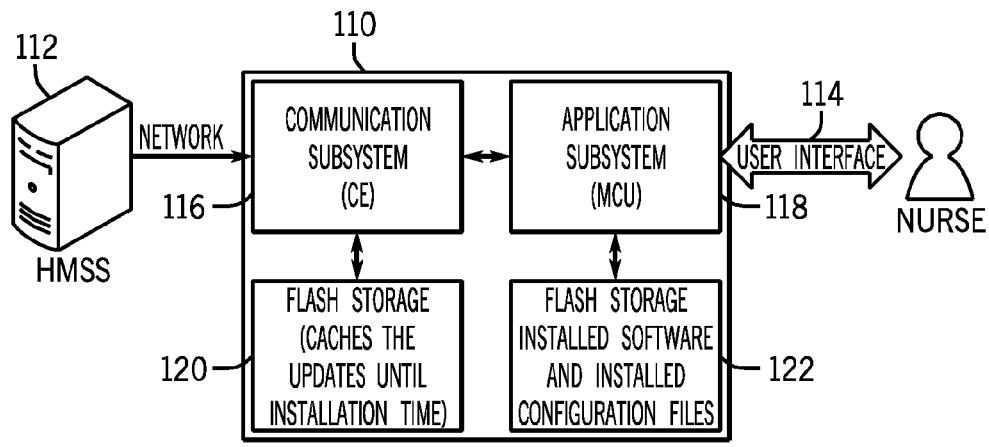
FIG. 10 is a block diagram of an infusion pump system.

FIG. 10 is an infusion pump system block diagram. FIG. 10 shows an infusion pump 110 (i.e., an infuser) and a Hospira MedNet™ server 112 or HMSS coupled by a computer network, allowing the server and infusion pump to communication with one another. The infusion pump 110 includes a user interface 114, allowing a nurse, or other user, to monitor and/or operate the infusion pump 110. The infusion pump 110 includes a communication subsystem 116 (i.e., a communication engine) and an application subsystem 118 (i.e., an MCU (master control unit)), as shown. The communication subsystem 116 has access to flash storage 120 for caching updates until installation time. The application subsystem 118 has access to flash storage 122 for storing installed software and configuration files.

Figure 11:
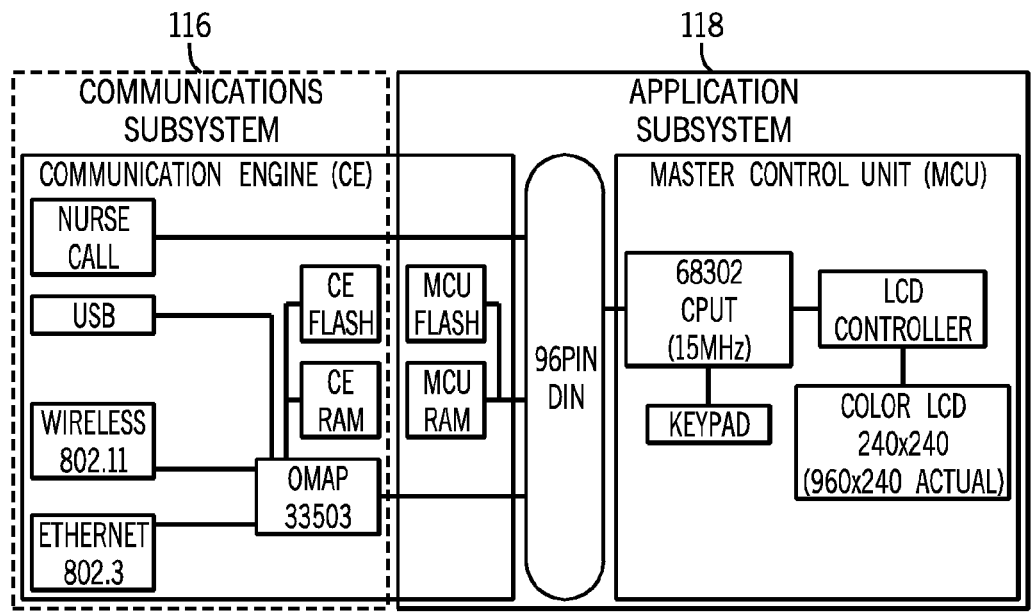
FIG. 11 is a block diagram of an infusion device physical/subsystem.

FIG. 11 is an infusion device physical/subsystem block diagram illustrating the physical arrangement of some features of the infusion pump communication subsystem 116 and application subsystem 118. Both subsystems have access to RAM and flash memory. The communication subsystem 116 includes interfaces to outside systems (wired and wireless). The MCU of the application subsystem 118 includes a CPU, and also provides control of the pumping action, as well as the user interface devices.

Figure 12:
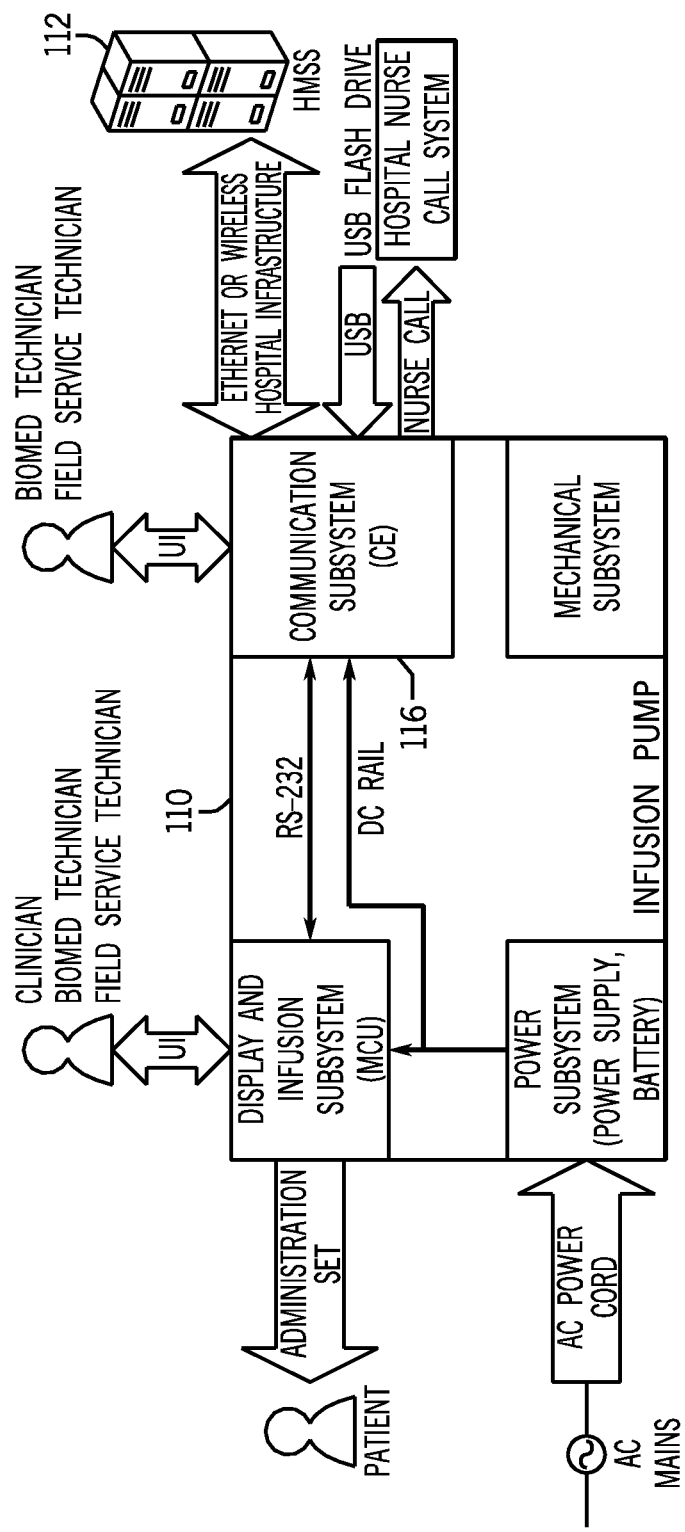
FIG. 12 is a block diagram of an infusion pump system architecture.

FIG. 12 is an infusion pump system architecture block diagram. FIG. 12 shows an infusion pump 110, including the communication subsystem 116, which provides a communication interface with the server 112 and a hospital nurse call system. The infusion pump 110 also includes a mechanical subsystem, a power subsystem, and a display and infusion subsystem (part of the MCU).

Like the examples described above, the infusion pump system illustrated in FIGS. 10-12 is capable of handling updates to the infusion pump software and to the drug library. When the communication subsystem 116 receives an update request from the server 112, the received message will contain a manifest of files which make up the update. In this example the update will be for a drug library or software and a drug library.

In most cases, a software update will come with a new custom library. In this case, when a new software update is provided, the update will comprise a matched set, including a software update and a drug library update, since the drug library is closely tied to the application and a change in the software affects the drug library. In some examples, the system is configured to not allow receiving just software without a custom drug library prepared with the drug library editor (DLE) application. This is controlled by the server.

The received manifest also includes the network location (path) to each of the files in the update. The communication subsystem is responsible for downloading the update files, verifying them, and storing them locally in communication subsystem flash. The communication subsystem will then notify the MCU that there is a custom drug library or software update and a drug library to transfer and install.

It is important to note that, in this example; the communication subsystem is running and possibly connected to the server when the infuser is plugged into AC power. Powering off the infuser while plugged into AC power will only power off MCU—the communication subsystem will continue to operate, enabling updates to be transferred to and installed on the medical device even when the medical device is powered off.

Once informed of a pending drug library update, the MCU will cause a screen on the infuser to display when the user attempts to power off the infuser. This screen gives the user a choice to install the drug library at that time, or to defer the installation to a later time. If the user chooses to install the drug library, the AC power status is first verified (to reduce the chances power loss during the installation) and the communication subsystem will transfer the data to MCU. When the transfer is complete, the installation process will continue without operator input.

If the user chooses not to install the drug library, the MCU will power down without installing the new drug library. The user will continue to be notified that there is a drug library update available each time the infuser is powered down until the drug library is ultimately installed.

In the case of an installation failure, the user will be alerted with a failure screen on the subsequent power on. The operator may then re-attempt the installation by powering off the infuser, or may continue to operate with the previous custom drug library.

Figure 13:
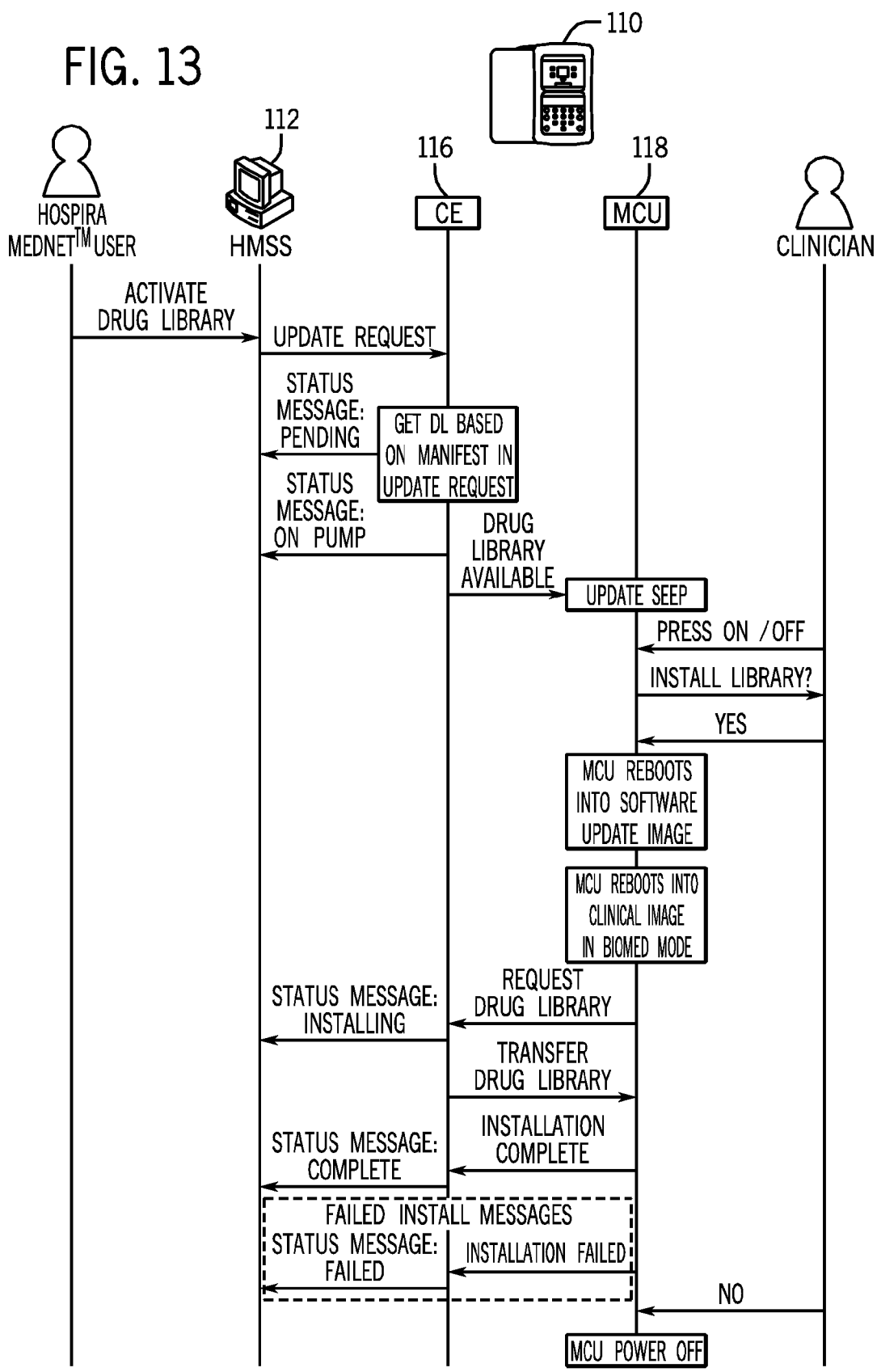
FIG. 13 is a sequence diagram showing the exchange for a library download, transfer, and installation.

FIG. 13 is a sequence diagram showing the exchange for a drug library download, transfer and installation. As shown, a Hospira MedNet™ user activates a drug library for one or more infusion pumps. In response, the server 112 generates and sends an update message for the medical device 10. The communication subsystem 116 receives the update message and in response, downloads the drug library update files (checking any files it already has against the manifest in the update). Once the files are downloaded and verified, the communication subsystem 116 will send a message to the application subsystem 118, indicating that an update is available.

During the shutdown of the infuser, the MCU will ask the user whether the updates should be installed. If the user accepts, the MCU reboots into a software update image. The MCU then reboots into a clinical image in a biomed mode. Next, after a request, the drug library is transferred from the communication subsystem to the MCU and installed. Finally, the infuser will shutdown. During this process, the infuser will provide status messages to the server 112, indicating the status of the update process (e.g., files successfully downloaded, download failed, update complete, update failed, etc.).

The process for updating MCU software is similar to the custom drug library installation insomuch as it occurs when the operator powers down the infuser. At that point, the communication subsystem will have received and verified the software and or drug library against the information sent from the server (the manifest file with checksums, and version information for the packages to install). The communication subsystem will advertise this new software and custom drug library to the MCU across its serial interface. The MCU will mark this in a special memory location called SEEP—Serial EEPROM in FIG. 14).

When the infuser is powered down (based on a user pressing the On/Off button) a screen will be displayed by the MCU offering to begin the software installation process.

Figure 14:
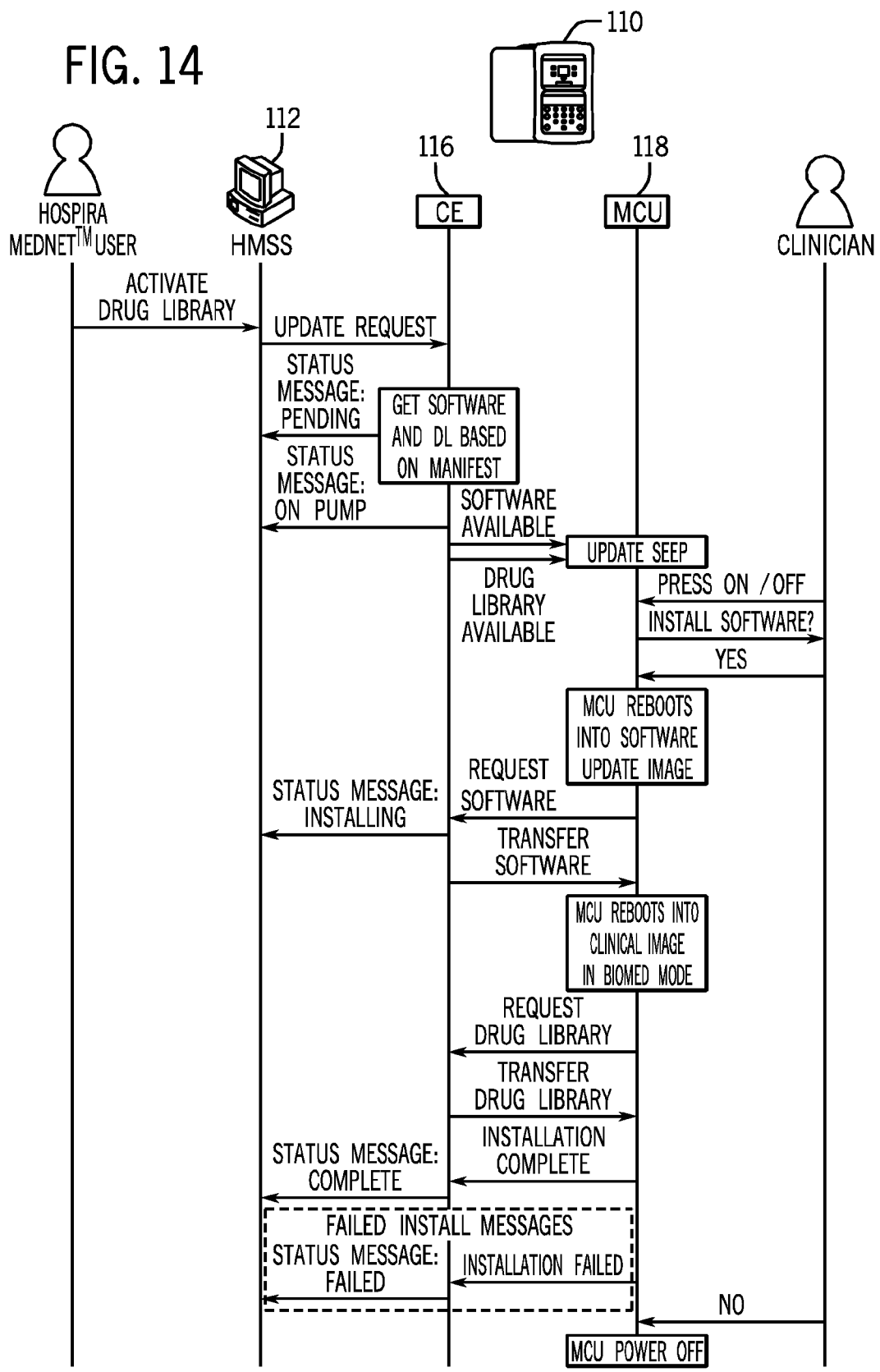
FIG. 14 is a sequence diagram showing the exchange for a software and library download, transfer, and installation.

FIG. 14 is a sequence diagram showing the exchange for a software and library download, transfer and installation. As shown, a Hospira MedNet™ software user activates a drug library for one or more infusion pumps. In response, the server 112 generates and sends an update message for the medical device 10. The communication subsystem 116 receives the update message and in response, downloads the software and drug library update files (checking any files it already has against the manifest in the update). Once the files are downloaded and verified, the communication subsystem 116 will send a message to the application subsystem 118, indicating that software and drug library updates are available.

During the shutdown of the infuser, the MCU will ask the user whether the updates should be installed. If the user accepts, the MCU reboots into a software update image. Next, after a request, the software is transferred from the communication subsystem to the MCU. The MCU then reboots into a clinical image in a biomed mode. Next, after a request, the drug library is transferred from the communication subsystem to the MCU and the updates are installed. Finally, the infuser will shutdown. During this process, the infuser will provide status messages to the server 112, indicating the status of the update process (e.g., files successfully downloaded, download failed, update complete, update failed, etc.).

Note that if there is a software update for the communication subsystem as part of the software update package from the server, the communication subsystem update will install first before the software will install on the MCU. In any case, the last thing installed from a software update package will be the custom drug library for the MCU.

As discussed above with respect to FIG. 8, to ensure the continued proper operation of an infuser, precautions should be taken to maintain its proper operation. For example, an infuser may not operate without a correct configuration. Therefore, special care can be taken to preserve the previous configuration when a configuration update installation fails. In one example, when updates are transferred from the communication subsystem, until they are successfully received and committed to flash, the previous configuration remains in effect.

Figure 15:
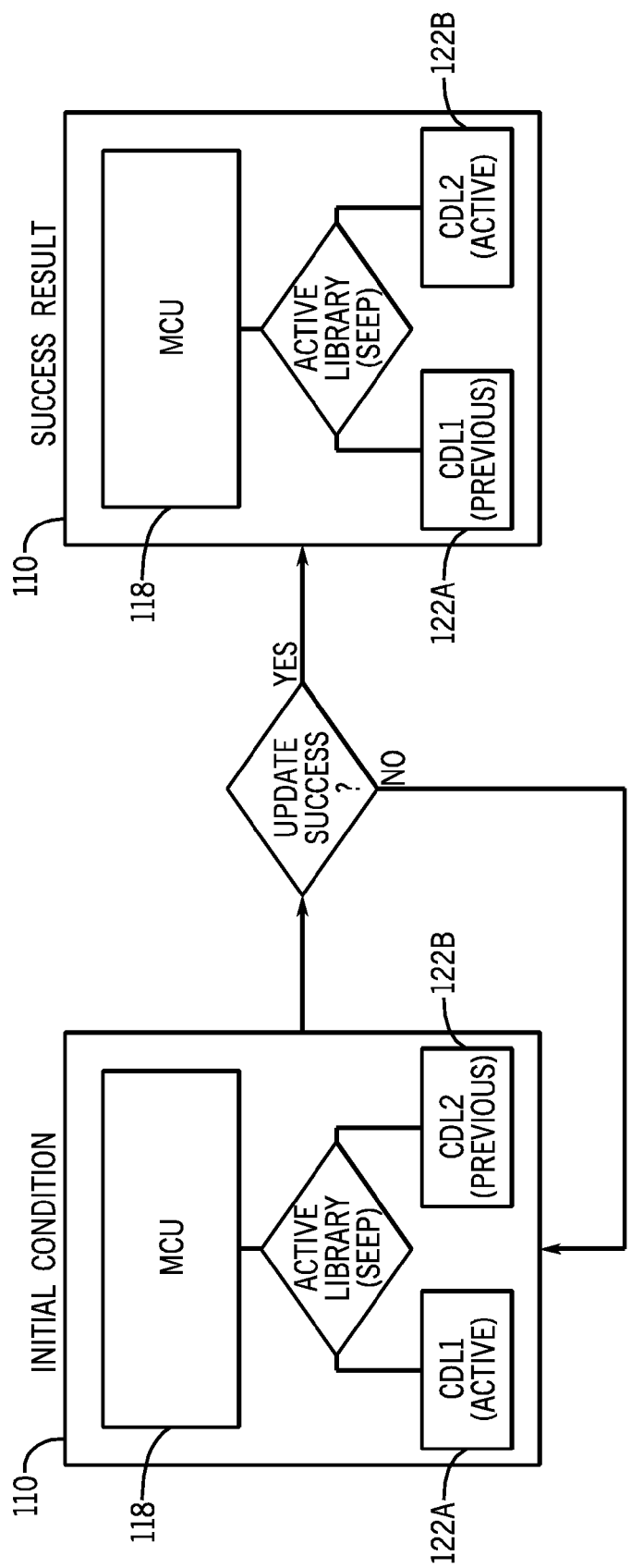
FIG. 15 is a diagram and flow chart illustrating the state of an infuser before and after an attempted update.

FIG. 15 is a diagram and flow chart illustrating the state of an infuser before and after an update is attempted. As shown, the MCU 118 maintains two drug library locations 122A and 122B in its flash memory. The SEEP controls which is the active library. As new libraries are loaded onto the MCU, the previous active library is maintained as a failover option. When new software is installed on the MCU, all previous custom drug libraries are erased as the format may have changed. As a part of the installation process for new software, the default drug library which comes with the new software is copied to one of the custom drug library (CDL) locations and SEEP is updated with this information as the active library. The communication subsystem will send the custom drug library, which is part of the update package, and the MCU will store the custom drug library in the unused custom drug library flash location and update SEEP with the newly stored custom drug library as the active CDL.

Subsequent updates will then cause the oldest library to be replaced with the new library and updates to SEEP will control which is the active library on the next power up.

If a custom drug library installation fails there will be no update in SEEP, so the previous active drug library will continue to be the active drug library. When the user next powers the MCU off, the drug library install screen will again offer to install this or any newly delivered custom drug library.

FIGS. 16-19 are diagrams illustrating processes for updating drug libraries and software, from the perspective of a user of the device. FIGS. 16-19 illustrate walkthroughs that provide the important points of a user's experience and show the sequence and state information as the process is preformed for the custom drug library installation and software installation, as well as the failure processing when an update operation fails.

Figure 16:
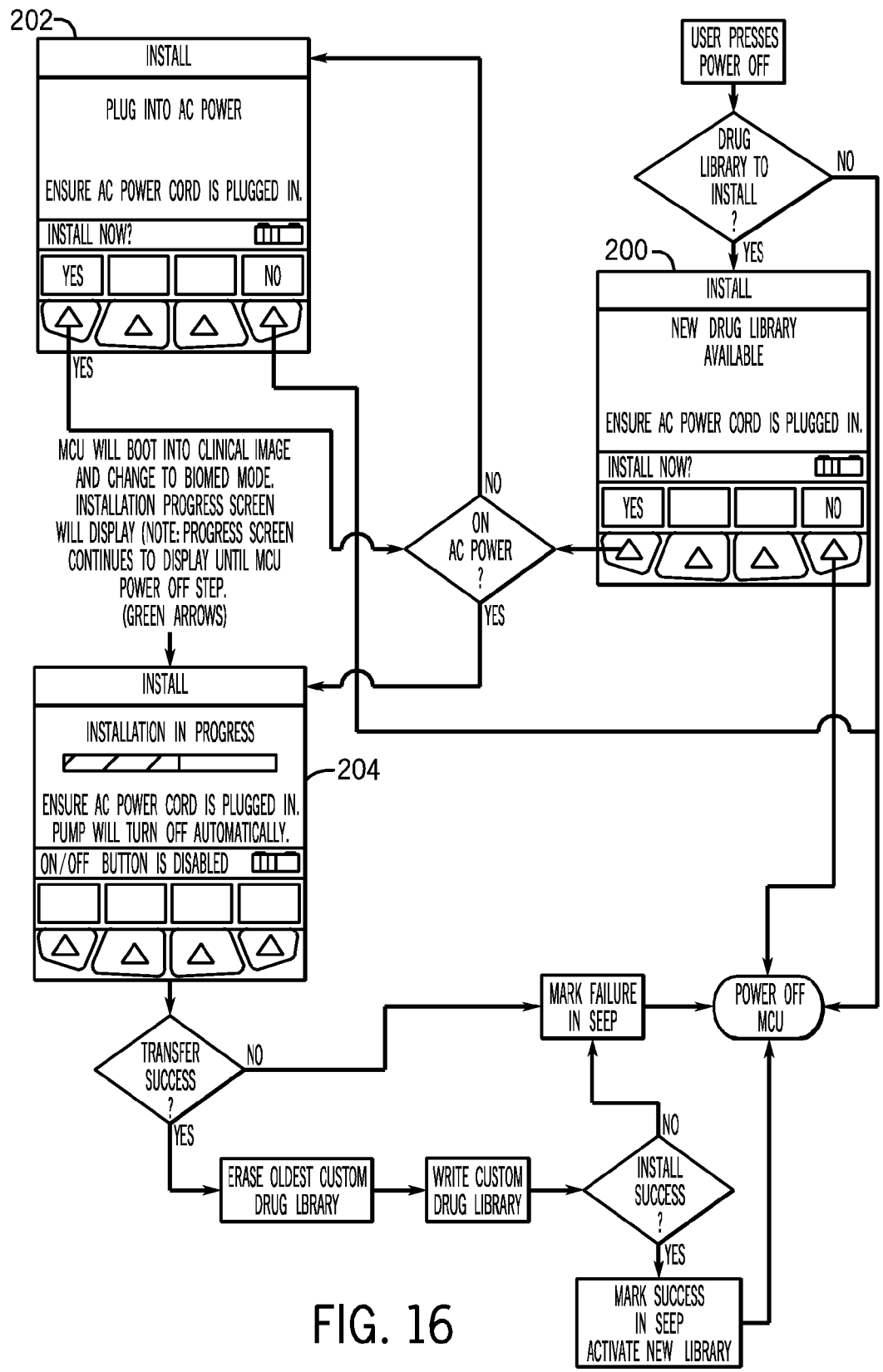
FIGS. 16-19 are diagrams illustrating processes for updating drug libraries and software, from the perspective of a user.

FIG. 16 illustrates an infuser screen walkthrough for a drug library installation, showing the steps and screens which will occur during the drug library transfer and installation process. The process begins when the user presses the power off button. If there is a drug library ready to be installed, screen 200 appears, and the user is asked to install the update. If the user selects "No", to MCU powers off. If the user selects "yes", the system verifies whether the infuser is plugged into AC power. If not, window 202 appears, telling to user to plug the unit it. Next, screen 204 appears, and the installation begins. If the transfer is successful, the oldest drug library is erased and the new library is written to memory. Next, the SEEP memory is marked as either a success or failure, and the MCU is powered off.

Figure 17:
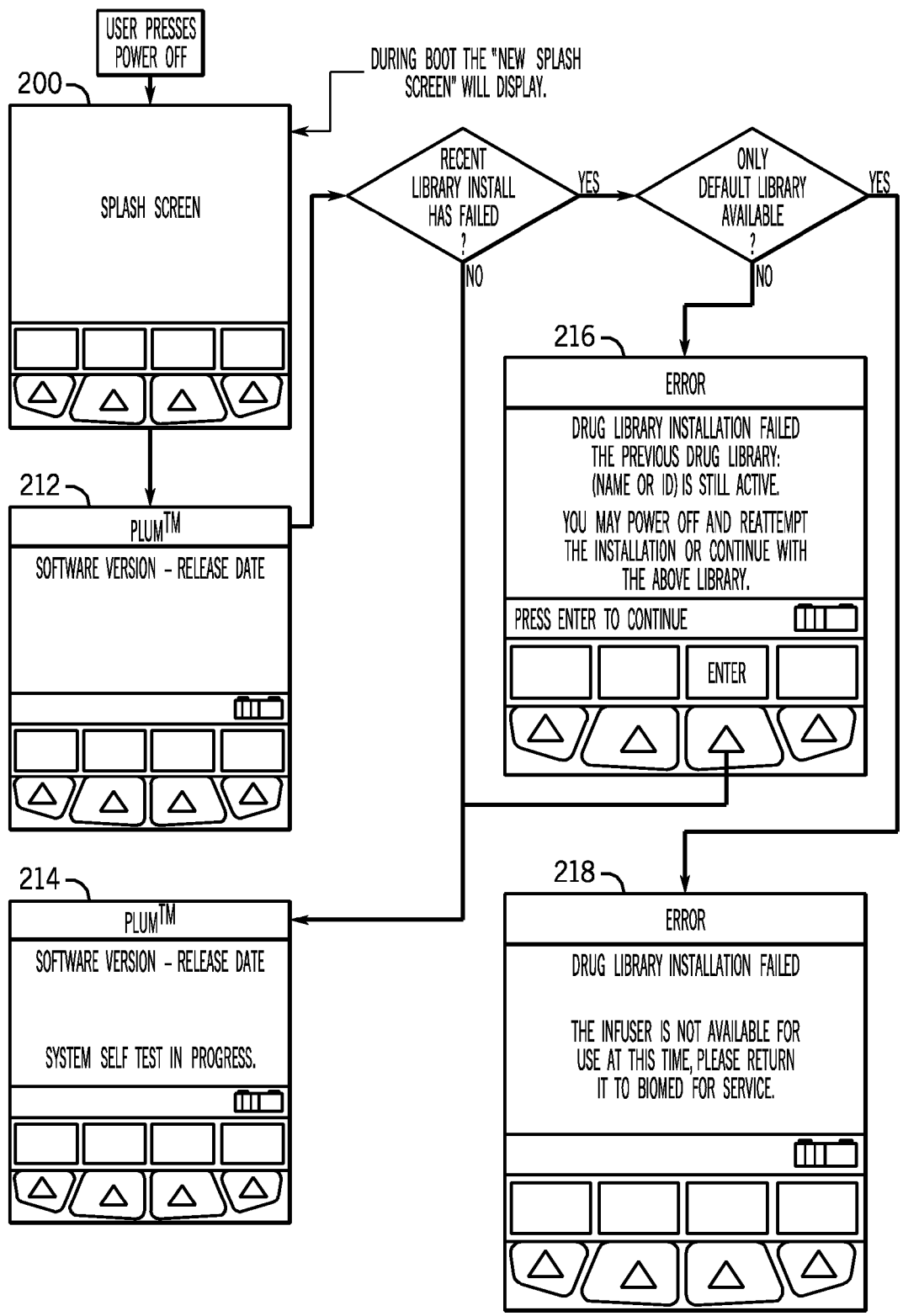

FIG. 17 illustrates an infuser screen walkthrough for a failed drug library installation. The screenshots of FIG. 17 show the steps and screens which result from a failed Library installation during subsequent power on processing. The drug libraries on the infuser are stored such that if a new drug library fails to install correctly the previous library is available and is used until the user can reattempt the installation. However if the only previous drug library available is the default drug library then the infuser is not available for use. This will be the case if new software is installed and the custom drug library that came as part of the software update fails to install correctly.

The process begins when the user presses the power on button, and the splash screen 210 appears. If the install was successful, or if the user pressed the 'Enter' button on a failed screen where the only remaining library is not the default library, then the normal flow of screens (screens 212, 214) will be displayed. After a failed installation, either error screen 216 (where the user has the option of using the previously installed drug library) or screen 218 (where the infuser will be inoperable) will appear.

Figure 18:
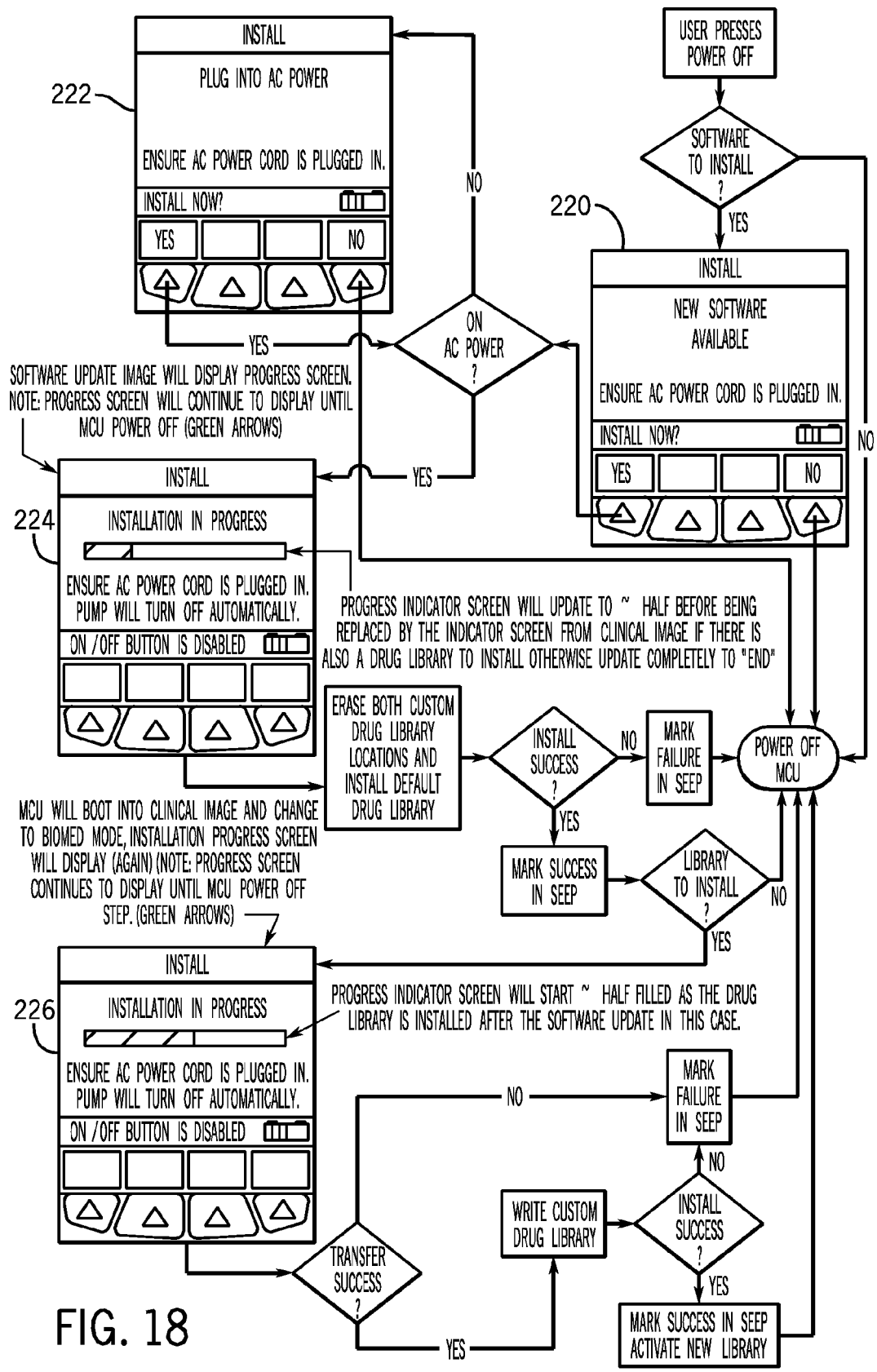

FIG. 18 illustrates an infuser screen walkthrough for a software installation process. The screenshots of FIG. 18 show the steps and screens which result in the processing for the installation process. In the case of a failure the process will repeat until successful or for three failed attempts.

When the user presses the power off button, and there is software ready to be installed, screen 220 will appear, asking the user to install the software. If the user selects "No", to MCU powers off. If the user selects "yes", the system verifies whether the infuser is plugged into AC power. If not, window 222 appears, telling to user to plug the unit into an AC power source. Alternatively, in another embodiment the installation can proceed with battery or DC power alone. Next, screen 224 appears, and the software installation begins, and both custom library locations are erased. If the software installation failed, the failure is marked in the SEEP memory, and the MCU powers off. If the software installation was successful, screen 226 appears, and the drug library installation begins. If the library installation failed, the failure is marked in the SEEP memory, and the MCU powers off. If the library transfer was successful, the custom drug library is written to memory. Next, the SEEP memory is marked as either a success or failure, and the MCU is powered off.

Figure 19:
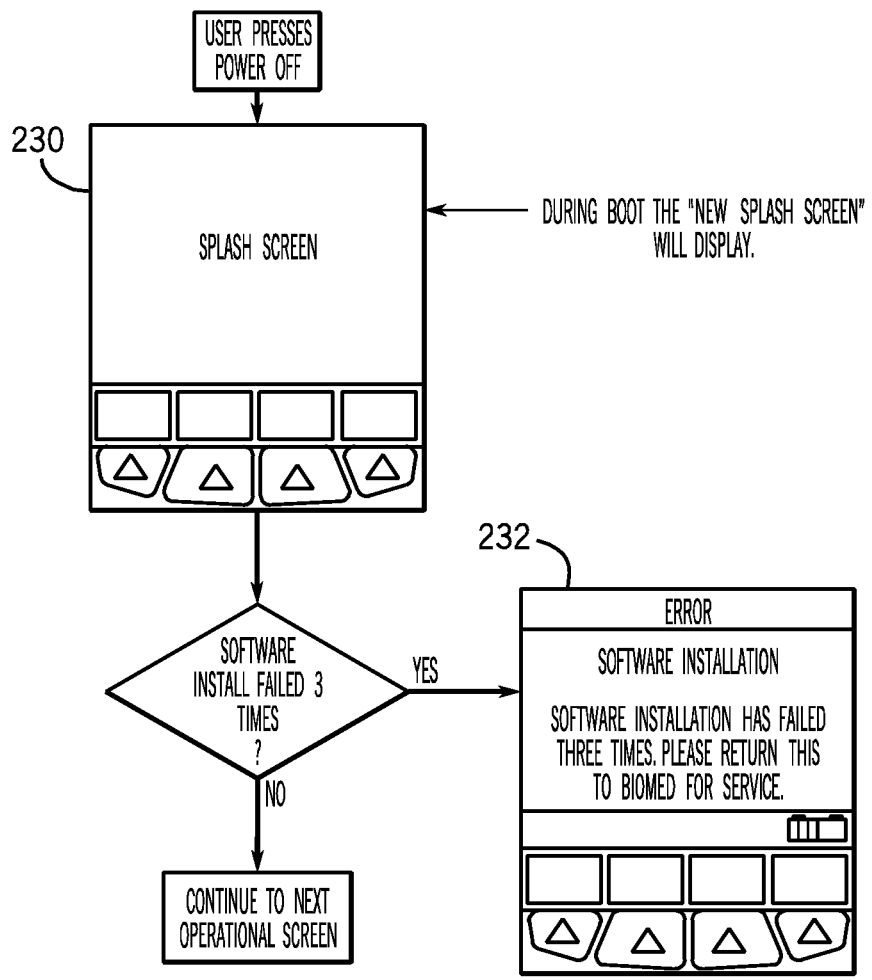

FIG. 19 illustrates an infuser screen walkthrough for a failed software installation. After a user presses the power on button, splash screen 230 appears. If the software installation has failed 3 times (in this example), screen 232 appears, instructing the user to return the infuser to the biomed center for service. If the software has not failed 3 times, the software update process can be repeated.

As described above, updates will be available to medical devices after a user goes through a selection process to selects one or more updates for one or more medical devices. In one example, a wizard-based selection mechanism is provided to allow any number of the devices to be selected for updates. The wizard can run on the server, or on a network client that communicates with the server.

Figure 20:
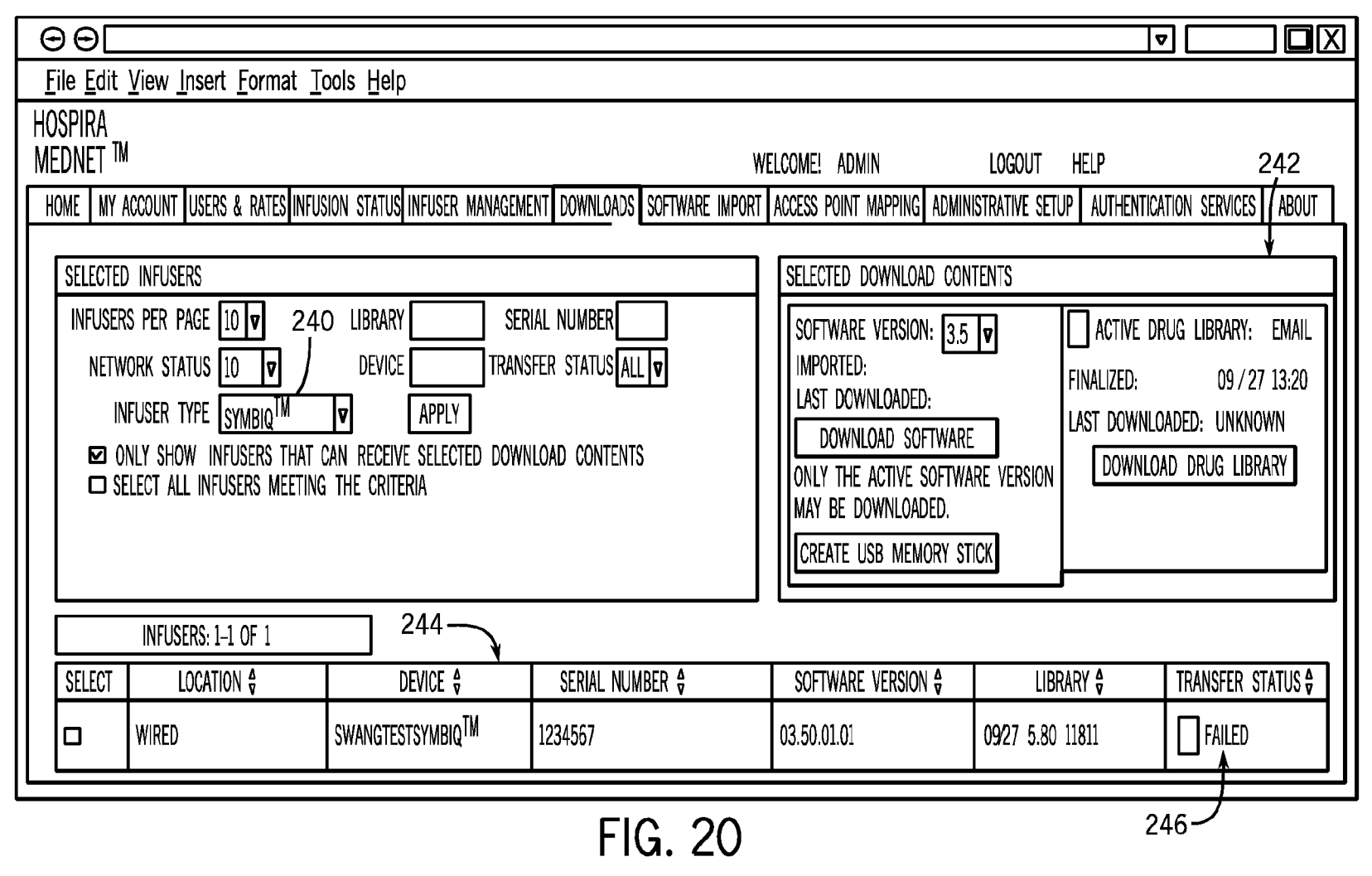

FIG. 20 is a screenshot of an exemplary selection wizard used by a user to select updates and devices for updates. Using the wizard, an IT technician can configure an update on the server. The wizard is flexible enough to allow for many different implementations. In this example, a type of device is selected (pull down menu 240) and the available software and configuration files are presented (box 242). The IT technician can then select the devices (displayed in table 244) to update and which files will be part of the update. The server will package the update into some number of files, implemented as JAR zip compressed files, in one example. The screen will also display the status 246 of the updates during the update process.

The update message (described above) is prepared for the devices. The update message contains a manifest or list of the files and their locations on the server. The update may be a single file on one server or can be composed of multiple files from multiple servers or locations on one server. The server will send this message to each of the selected devices informing the devices of the availability and location of the update(s).

As described above, the devices will then pull the update file(s) from the server(s) and store the update locally on the device. The device will then prompt the nurse during power off to install the update. The update will install and then the device will power down normally. A scripting interface in the update may make the updates available at a future time allowing for staged delivery of the updates to all the devices before the update is made available.

In the preceding detailed description, the disclosure is described with reference to specific exemplary embodiments thereof. Various modifications and changes may be made thereto without departing from the broader scope of the disclosure as set forth in the claims. The specification and drawings are, accordingly, to be regarded in an illustrative rather than a restrictive sense.

What is claimed is:

1. A method of providing updates to a medication administering device, the method comprising:
    a server sending an update message to the medication administering device relating to one or more update files available to the medication administering device, the update message containing a manifest, the manifest including the location of the update files available to the medication administering device, update file version information, and update file integrity verification information;
    receiving the update message at the medication administering device;
    while the medication administering device is being used to administer medication, downloading one or more update files identified by the update message;
    using the update file integrity verification information to verify that the one or more update files were successfully downloaded;
    storing the one or more update files on the medication administering device in a first memory location for installation at a future time;
    storing a currently used device software file and a currently used drug library file of the medication administering device in a second memory location on the medication administering device for recovery purposes;
    prompting a user of the medication administering device to update the medication administering device;
    upon the user accepting the update prompt, installing the one or more update files on the medication administering device;
    wherein the update files include one or more of updated device software and an updated drug library, and the step of prompting the user of the medication administering device to update the medication administering device includes the sub-steps of 1) prompting the user to install the updated device software, and then 2) prompting the user to install the updated drug library only upon successful installation of the updated device software.

2. The method of claim 1, wherein updates are provided to a plurality of medication administering devices, the method further comprising:
    selecting one or more medication administering devices to be updated; and
    receiving an update message at the selected medication administering devices.

3. The method of claim 2, wherein the one or more medication administering devices are selected based on one or more of: the physical location of a device, the model of the device, the type of device, and the way the device is being used.

4. The method of claim 1, wherein the downloaded update files are stored in a storage location of the medication administering device, and wherein the first memory location or second memory location also stores one or more previous versions of the update files to be updated.

5. The method of claim 1, wherein the update files include a script used for orchestrating an update process.

6. The method of claim 1, wherein the update message is sent and the update files are retrieved using a communications network.

7. The method of claim 1, wherein the update message is sent and update files are retrieved by the medication administering device using one or more portable storage devices.

8. The method of claim 1, further comprising providing status messages to a server, the status messages relating to downloading and installing of updates.

9. The method of claim 1, wherein the update message received at the medication administering device is a message unique to that device.

10. The method of claim 1, wherein the medication administering device includes at least one infusion pump.

11. The method of claim 1, comprising the medication administering device determining whether the medication administering device is connected to AC power, prompting the user to connect the medication administering device to a source of AC power, and then continuing with installing the one or more update files once the medication administering device is connected to a source of AC power.

12. The method of claim 1, comprising attempting installation of an update file multiple times before declaring an installation activity unsuccessful.

13. The method of claim 12, comprising prompting the user to send the medication administering device to a biomedical engineer upon three consecutive failed attempts of installing the updated device software.

14. A medical device system comprising:
a server;
a communication network; and
a plurality of medical devices in communication with the server over the communication network, the plurality of medical devices each having a first storage location and a second storage location, and a control unit for controlling the operation of the medical device, wherein the control units are configured to:
receive an update message from the server, the update message containing a manifest, the manifest including the location of update files available to the medical device, update file version information, and update file integrity verification information;
while the medical device is being used to administer medication, pull the update files in response to the update message received from the server;
using the update file integrity verification information to verify that the update files were successfully downloaded;
store the update files in the first storage location on the medical device for installation at a future time; and
store a currently used device software file and a currently used drug library file of the medical device in a second storage location on the medical device for recovery purposes;
prompt users of respective medical devices to update the respective medical device, wherein the control units are configured to manage the installation of downloaded update files upon acceptance of the update prompt by the user, and wherein the update files include one or more of updated device software and an updated drug library, and the step of prompting the user of the medical device to update the medical device includes the sub-steps of 1) prompting the user to install the updated device software, and then 2) prompting the user to install the updated drug library only upon successful installation of the updated device software.

15. The medical device system of claim 14, wherein the medical device system is configured such that a user can select one or more of the medical devices to be updated.

16. The medical device system of claim 15, wherein medical devices are selected based on one or more of: the physical location of a device, the model of the device, the type of device, and the way the device is being used.

17. The medical device system of claim 14, wherein each respective first storage location stores downloaded update files and each respective second storage location is adapted to store one or more previous versions of files to be updated.

18. The medical device system of claim 14, wherein each respective update file of the update files includes a script used for orchestrating an update process.

19. The medical device system of claim 14, wherein the control units are configured to provide status messages to the server, the status messages relating to downloading and installing update files.

20. The medical device system of claim 14, wherein the plurality of medical devices includes at least one infusion pump.

* * * * *